(12) United States Patent
Shibata et al.

(10) Patent No.: US 7,161,671 B2
(45) Date of Patent: Jan. 9, 2007

(54) METHOD AND APPARATUS FOR INSPECTING DEFECTS

(75) Inventors: Yukihiro Shibata, Fujisawa (JP); Shunji Maeda, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/885,077

(22) Filed: Jul. 7, 2004

(65) Prior Publication Data
US 2004/0257560 A1    Dec. 23, 2004

Related U.S. Application Data

(63) Continuation of application No. 10/279,790, filed on Oct. 25, 2002, now Pat. No. 6,762,831.

(30) Foreign Application Priority Data
Oct. 29, 2001 (JP) .............................. 2001-330113

(51) Int. Cl.
*G01N 21/00* (2006.01)

(52) U.S. Cl. .............................. 356/327.2; 356/237.5; 250/559.42

(58) Field of Classification Search .. 356/237.1–237.6, 356/394, 367–369; 250/559.42, 559.48, 250/548; 382/149; 182/149; 430/30; 219/121.68, 219/121.6
See application file for complete search history.

(56) References Cited

U.S. PATENT DOCUMENTS

| | | | |
|---|---|---|---|
| 4,595,289 A * | 6/1986 | Feldman et al. | 356/237.5 |
| 4,769,523 A * | 9/1988 | Tanimoto et al. | 219/121.6 |
| 4,974,919 A * | 12/1990 | Muraki et al. | 359/204 |
| 5,038,048 A * | 8/1991 | Maeda et al. | 250/559.41 |
| 5,278,012 A | 1/1994 | Yamanaka et al. | |
| 5,430,548 A | 7/1995 | Hiroi et al. | |
| 5,479,252 A | 12/1995 | Worster et al. | |
| 5,649,022 A * | 7/1997 | Maeda et al. | 382/141 |
| 5,764,363 A | 6/1998 | Ooki et al. | |
| 5,774,222 A * | 6/1998 | Maeda et al. | 356/394 |
| 5,783,342 A | 7/1998 | Yamashita et al. | |
| 5,822,055 A * | 10/1998 | Tsai et al. | 356/237.1 |
| 6,031,201 A * | 2/2000 | Amako et al. | 219/121.68 |
| 6,034,776 A * | 3/2000 | Germer et al. | 356/369 |
| 6,256,092 B1 * | 7/2001 | Tomita et al. | 356/237.1 |
| 6,263,099 B1 | 7/2001 | Maeda et al. | |
| 6,268,093 B1 * | 7/2001 | Kenan et al. | 430/30 |
| 6,369,888 B1 * | 4/2002 | Karpol et al. | 356/237.5 |
| 6,400,454 B1 | 6/2002 | Noguchi et al. | |
| 6,546,308 B1 * | 4/2003 | Takagi et al. | 700/121 |

(Continued)

FOREIGN PATENT DOCUMENTS

JP    61189515 A  *  8/1986

(Continued)

*Primary Examiner*—Gregory J. Toatley, Jr.
*Assistant Examiner*—Sang H. Nguyen
(74) *Attorney, Agent, or Firm*—Antonelli, Terry, Stout and Kraus, LLP.

(57) ABSTRACT

Laser lights having a plurality of wavelengths from DUV to VUV range are used to inspect defects of a pattern at high speeds and in a high sensitivity using high light-output lasers, while solving a temporal/spatial coherence problem caused by using lasers as light source. This reduces the laser light temporal/spatial coherence. Further, to correct chromatic aberration caused by illumination with VUV and DUD lights, the lights of the VUV and DUV wavelengths are arranged in a coaxial illumination relation. The chromatic aberration left uncorrected is detected such that a detection optical path is branched into two optical path systems corresponding to respective wavelengths and an image sensor is placed on an image plane of each wavelength.

13 Claims, 14 Drawing Sheets

U.S. PATENT DOCUMENTS 6,556,290 B1  4/2003  Maeda et al.
6,621,571 B1  9/2003  Maeda

FOREIGN PATENT DOCUMENTS

| | | |
|---|---|---|
| JP | 62-073141 | 4/1987 |
| JP | A-01-187437 | 7/1989 |
| JP | 03099482 A * | 4/1991 |
| JP | 4-111336 | 4/1992 |
| JP | A-05-281130 | 10/1993 |
| JP | 07-083844 | 3/1995 |
| JP | 7-318326 | 12/1995 |
| JP | 11-311608 | 11/1999 |
| JP | 2000-323542 | 11/2000 |
| JP | 2001-194323 | 7/2001 |

* cited by examiner

FIG. 2A
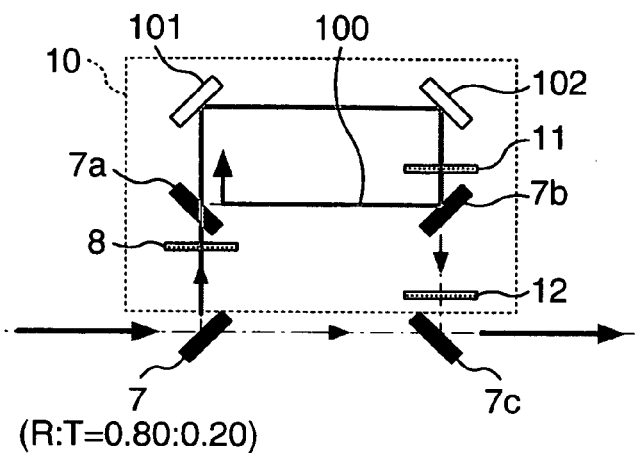
(R:T=0.80:0.20)
FIG. 2B
| CIRCULATING TIME | R | T |
|---|---|---|
| FIRST CIRCULATING TIME | 0.40 | 0.40 |
| SECOND CIRCULATING TIME | 0.20 | 0.20 |
| THIRD CIRCULATING TIME | 0.10 | 0.10 |
| FOURTH CIRCULATING TIME | 0.05 | 0.05 |
| ⋮ | ⋮ | ⋮ |
FIG. 3
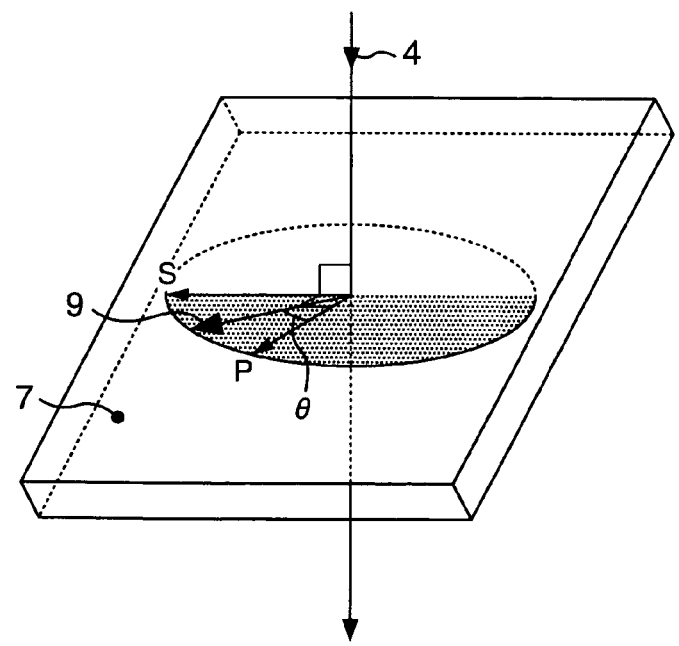

(DETECTED LIGHT
AMOUNT DISTRIBUTION
OF A-A PORTION)

(DETECTED LIGHT
AMOUNT DISTRIBUTION
OF A-A PORTION)

METHOD AND APPARATUS FOR INSPECTING DEFECTS

CROSS REFERENCE TO RELATED APPLICATION

This is a continuation of U.S. application Ser. No. 10/279,790, filed Oct. 25, 2002, now U.S. Pat. No. 6,762,831, the subject matter of which is incorporated by reference herein.

BACKGROUND OF THE INVENTION

The present invention is related to an optical system, a defect inspecting method and a defect inspecting apparatus with employment of this optical system, and a utilizing method for effectively utilizing inspection information, while the optical system is employed so as to inspect and observe defects and extraneous-material defects of patterns formed on substrates by way of thin-film manufacturing processes which are typically known in semiconductor manufacturing steps and manufacturing steps of flat panel displays.

To detect defects of very fine patterns formed on substrates by way of thin-film manufacturing processes, images having high image quality are necessarily required, the focuses and contrasts of which have been adjusted in high precision.

In the defect inspection field for instance, JP-A-2000-323542 discloses the image detecting method of objects as the conventional technique capable of acquiring such high grade images. This conventional technique is to detect images as follows. That is, while a broadband white light source is employed as a light source and focal points are defined at different places along a Z direction with respect to each of wavelength ranges of white light, two systems of image sensors are arranged in such a manner that the image sensors are focused onto both a surface layer and a rear plane of an object in the case that the object owns stepped portions. In two systems of these image sensors, focusing positions on the object planes are made different from each other along an optical axis direction in accordance with longitudinal chromatic aberration of an objective lens. As a consequence, images of different planes of the object are detected by the respective image sensors by utilizing the longitudinal chromatic aberration of the objective lens. It should be understood that as to a detecting optical path for two systems of the image sensors, band-pass filters are arranged in optical paths defined by that an optical path is branched and thereafter the branched optical paths are reached to the respective image sensors in such a manner that such light corresponding to the respective longitudinal chromatic aberration may penetrate through these band-bass filters.

The above-described conventional technique is directed to such a technical idea that images of different planes on a wafer are detected by employing two systems of the image sensors, and then images focused on the respective image sensors are employed. As a consequence, this conventional technique is not to produce a new image from the images detected by two systems of these image sensors, but is directed so as to select any one of the images detected from two systems of these image sensors so that this selected image is used in the defect inspection. However, in thin-film manufacturing processes typically known as semiconductors, flatting (planer) process operations are carried out as to wafer surfaces based upon the CMP (Chemical Mechanical Polishing) process operation. Thus, the thin-film manufacturing processes need not detect images at different heights on a wafer by employing the above-explained two image sensors. Also, even when stepped portions are formed on wafers, since structures of semiconductor logic products are complex, the selective use of such images detected by two systems of these image sensors cannot be employed.

To detect defects of very fine patterns in high precision, wavelengths of illumination light must be made shorter. Generally speaking, laser light sources are necessarily required in order to secure sufficiently large amounts of illumination light of light sources having short wavelengths for inspection purposes. However, in the case that such laser light sources are employed as illumination, interference problems of laser light may occurs. In other words, there are problems as to temporal/spatial coherence, problems of interference noises which are produced by thin-films formed on surfaces of samples, problems of contract between very fine patterns and background patterns, problems of illuminance fluctuations of pulse illumination light, and the like.

SUMMARY OF THE INVENTION

In accordance with the present invention, while a laser having a large light amount is employed, defects of patterns can be inspected in a high sensitivity by solving the above-described problems as to the temporal/spatial coherence occurred because of using the laser in the above-explained illumination light source.

In other words, the present invention is so arranged by that basic resolution of an optical system may be improved by shortening a wavelength of illumination light. The wavelength to be shortened is directed to DUV (Deep Ultra-Violet) light up to VUV (Vacuum Ultra-Violet) light. As a light source used in these wavelength ranges, there is an F2 laser (wavelength being 157 nm) as the VUV range. In order to employ these laser light as a defect inspecting optical system for illumination purposes, there are two technical aspects. As one technical aspect, brightness fluctuations of detected images and coherencies are reduced, which are caused in connection with film thickness fluctuations in optically transparent interlayer insulating films which are formed on a surface of an object. The brightness fluctuations caused by the film thickness fluctuations of the insulating films were reduced by employing such an arrangement that light having a plurality of wavelengths is illuminated. Also, a temporal coherence can be also reduced by illuminating the light having such plural wavelengths.

However, as to the light in the range from DUV to VUV, since a nitre material having high transmittance is restricted, for instance, in such a case that both the VUV light and the DUV light are coaxially illuminated, chromatic aberration cannot be corrected. As a consequence, while the light having the respective wavelengths is coaxially illuminated, such a chromatic aberration which cannot be corrected is detected in such a manner that a detection optical path is branched into two optical paths corresponding to the wavelengths, and then, image sensors are arranged on image planes of the respective wavelengths. As a result, as to an object plane (same plane) for a subject matter, two images are detected which are focused within two wavelength ranges. Since these two images are electrically synthesized with each other (namely, new image is produced by employing two images), it is possible to detect such an image having high resolution, from which noise could be reduced in view of defect inspection.

These and other objects, features and advantages of the invention will be apparent from the following more particular description of preferred embodiments of the invention, as illustrated in the accompanying drawings.

BRIEF DISCRIPTION OF THE DRAWINGS

FIGS. 2A and 2B are a front view for showing a basic structure of an optical path difference optical system using polarization and a table showing the number of circulating times in the circulating optional path and the ratio between reflected light (R) and transmitting light (T) at PBS 7c respectively.

FIG. 3 is a perspective view of a PBS for explaining a calculation of an amplitude of light which penetrates through the PBS.

Figure 14A:
Figure 14B:
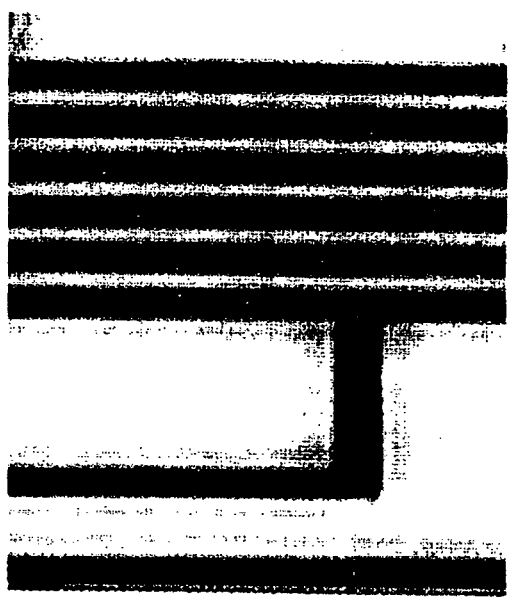

FIG. 14A indicates an image of a wiring pattern when is observed by a conventional optical system, and FIG. 14B shows an image of a wiring pattern which is observed by an optical system of the present invention.

Figure 15A:
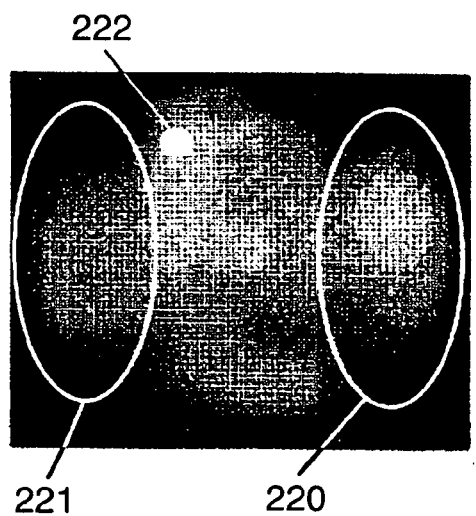
Figure 15B:
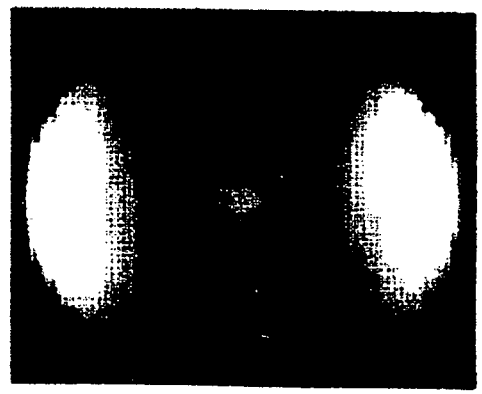

FIG. 15A represents an image of a focal position on the rear side of an objective lens in the case that a line-and-space pattern is observed by the conventional optical system, and FIG. 15B indicates an image of a focal position on the rear side of the objective lens in the case that the line-and-space pattern is observed by the optical system according to the present invention.

Figure 16:
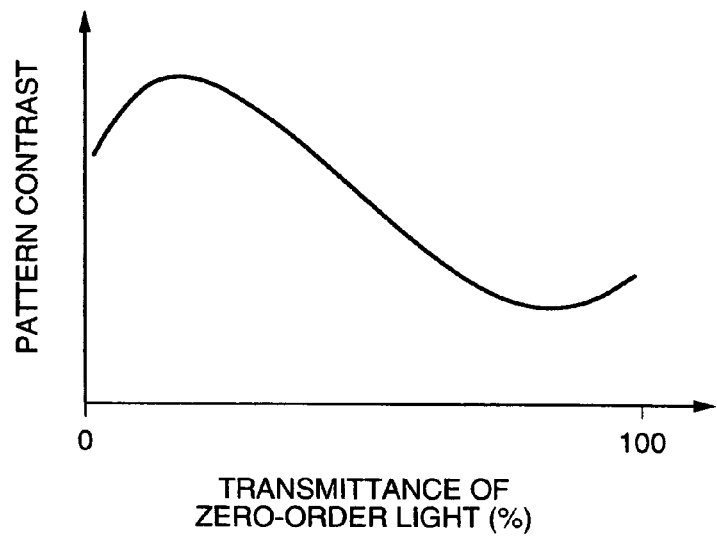

FIG. 16 is a graphic representation for indicating a relationship between transmittance of zero-order light and pattern contrast.

Figure 17A:
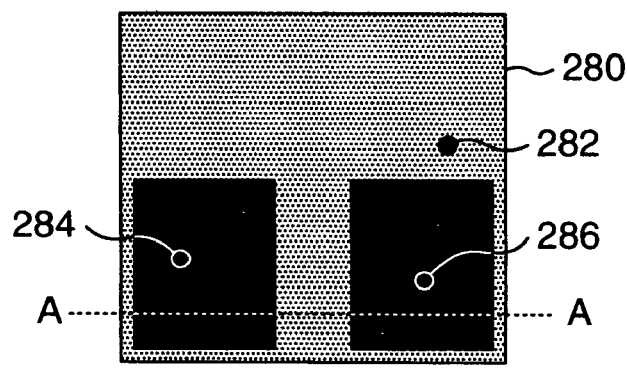
Figure 17B:
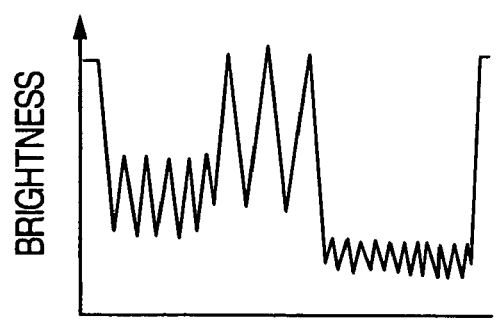
Figure 17C:
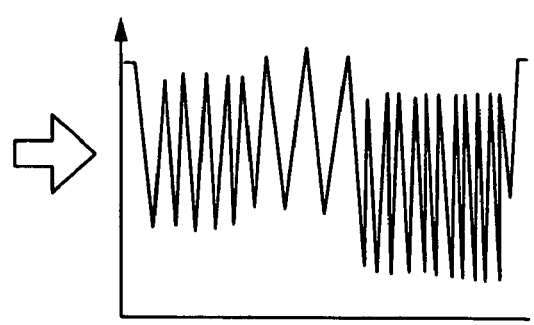

FIG. 17A is a plan view for representing a die formed on a wafer, FIG. 17B indicates a signal of a portion of an image of a die, taken along a line A—A of the die image, which is obtained when the die is observed by the conventional optical system, and FIG. 17C indicates a signal of a portion of an image of a die, taken along a line A—A of the die image, which is obtained when the die is observed by the optical system of the present invention.

Figure 18:
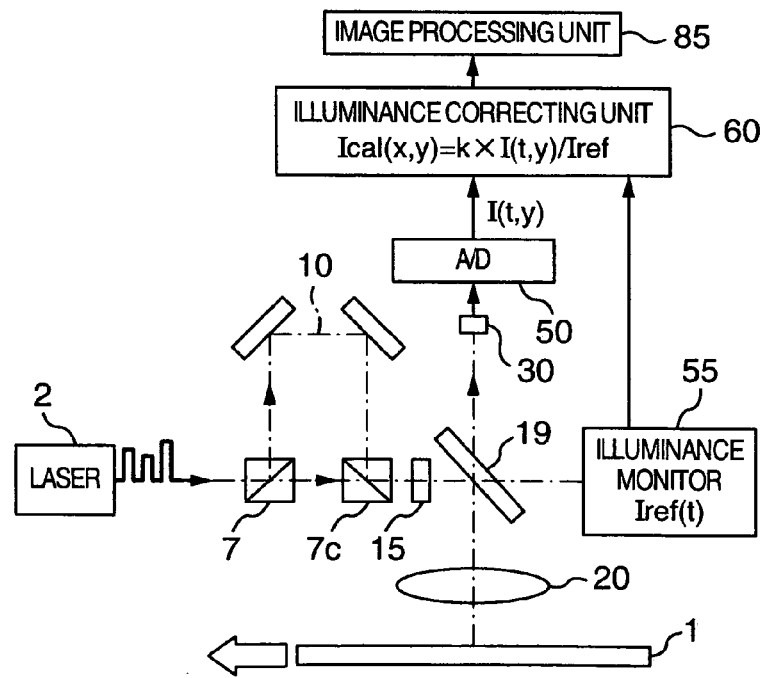

FIG. 18 is a schematic block diagram for showing an arrangement of an illuminance fluctuation correcting unit for illumination.

Figure 19:
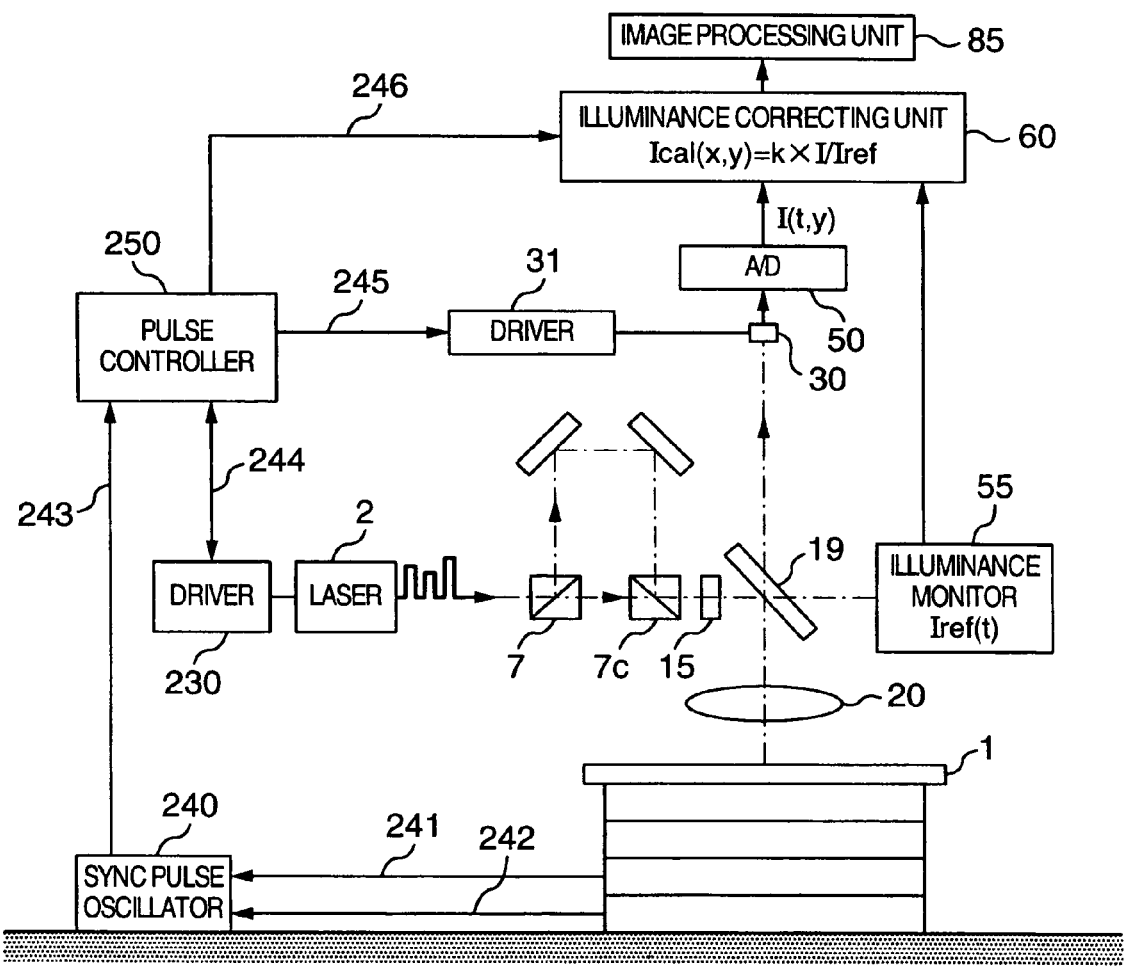

FIG. 19 is a schematic block diagram for indicating an arrangement of an observation optical system on which an illuminance fluctuation function is mounted.

Figure 20:
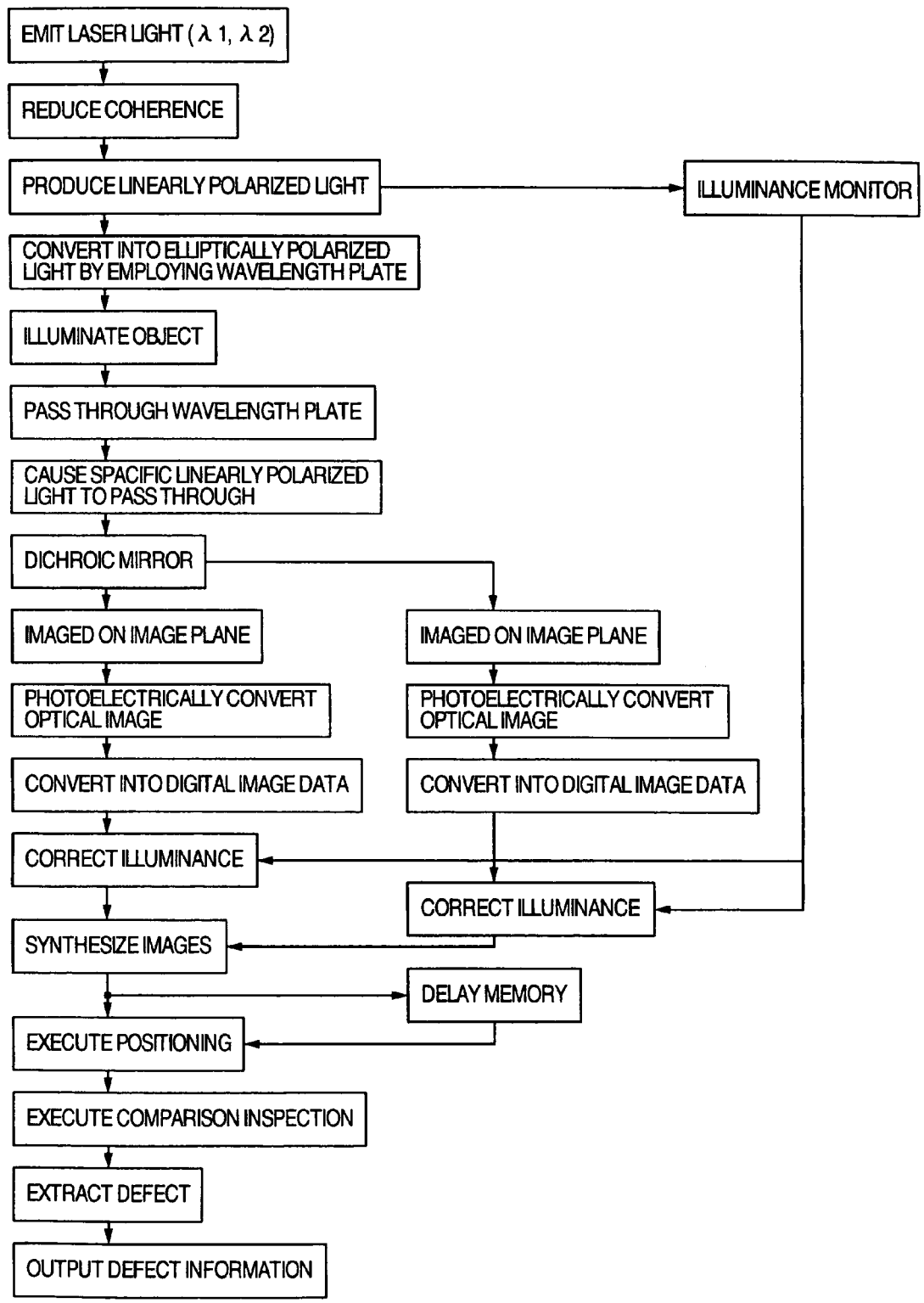

FIG. 20 is a flow chart for describing process flow operations of a pattern defect inspecting signal according to the present invention.

Figure 21:
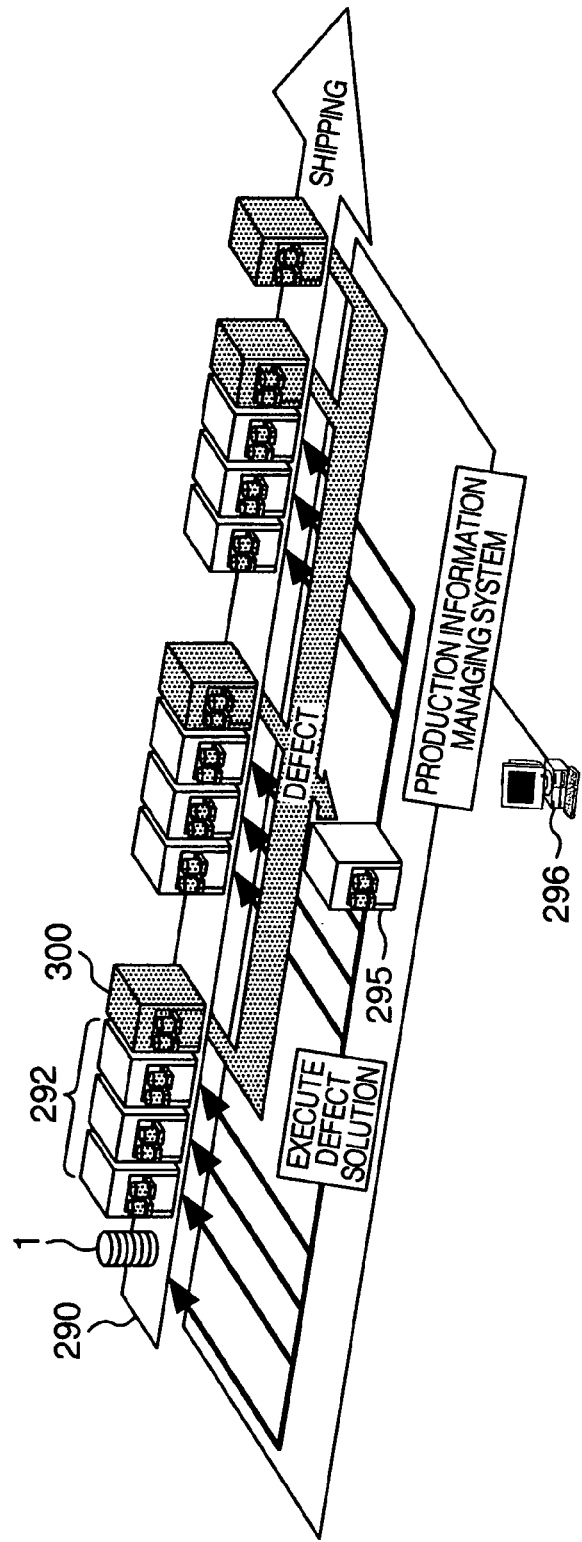

FIG. 21 is a perspective view for schematically indicating an arrangement of a production information managing system with employment of a defect inspecting apparatus according to the present invention.

Figure 22:
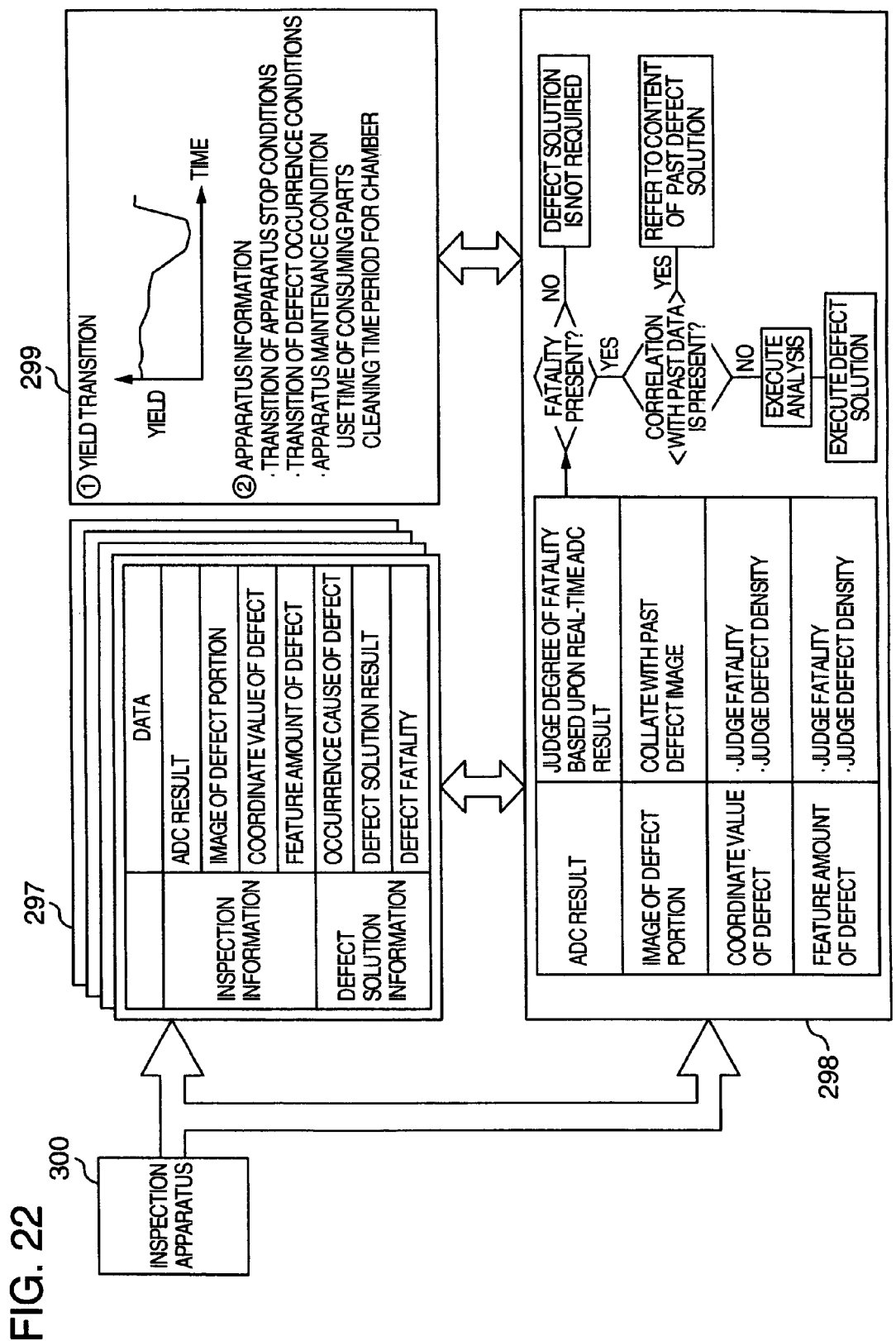

FIG. 22 is a diagram for showing an example of information of an inspection result which is outputted from the defect inspecting apparatus according to the present invention to the production information managing system.

DESCRIPTION OF THE EMBODIMENTS

In the present invention, light existing in the ranges from DUV (Deep Ultra-Violet) to VUV (Vacuum Ultra-Violet) is employed as illumination light so that the basic resolution may be increased. Inventors of the present invention have fined out such a fact that since polarization light is employed as illumination, even when very narrow defects occur, images having higher resolution (high contrast) may be acquired. However, when a laser light source is employed for illumination, a detection sensitivity would be lowered by receiving an adverse influence caused by so-called "stray light", namely laser light is reflected on a surface of an optical component and the reflected laser light is entered into a detector. In accordance with the present invention, in order to avoid this adverse influence of the lowered detecting sensitivity caused by this stray light, a plurality of optical paths having different optical path lengths are provided in an illumination optical system, and then, a detection is made of images produced by illumination light which passes through the respective optical paths to be reached on a sample.

Also, in order to reduce an adverse influence of a film thickness of an optically transparent film formed on a surface of a sample, such an arrangement is made. That is, as to chromatic aberration which cannot be corrected by a lens system, an optical path on a detection optical path is branched every wavelength, and images at the respective wavelengths are detected so as to realize a system for illuminating illumination light having a plurality of wavelengths from a coaxial direction. These images which have been detected every wavelength are synthesized with each other, and an image processing operation is carried out as to these synthesized images as a single image, so that a defect is detected. Also, in order that images can be detected which may give a merit for detecting a defect, an amplitude of zero-order light which is direct-reflected on a wafer is suppressed, and a balance between this suppressed amplitude of the zero-order light and an amplitude of high-order diffraction light can be adjusted. Furthermore, either Brewster angle illumination or total reflection angle illumination has been employed as an illumination system capable of reducing an adverse influence of thin-film interference.

Figure 1:
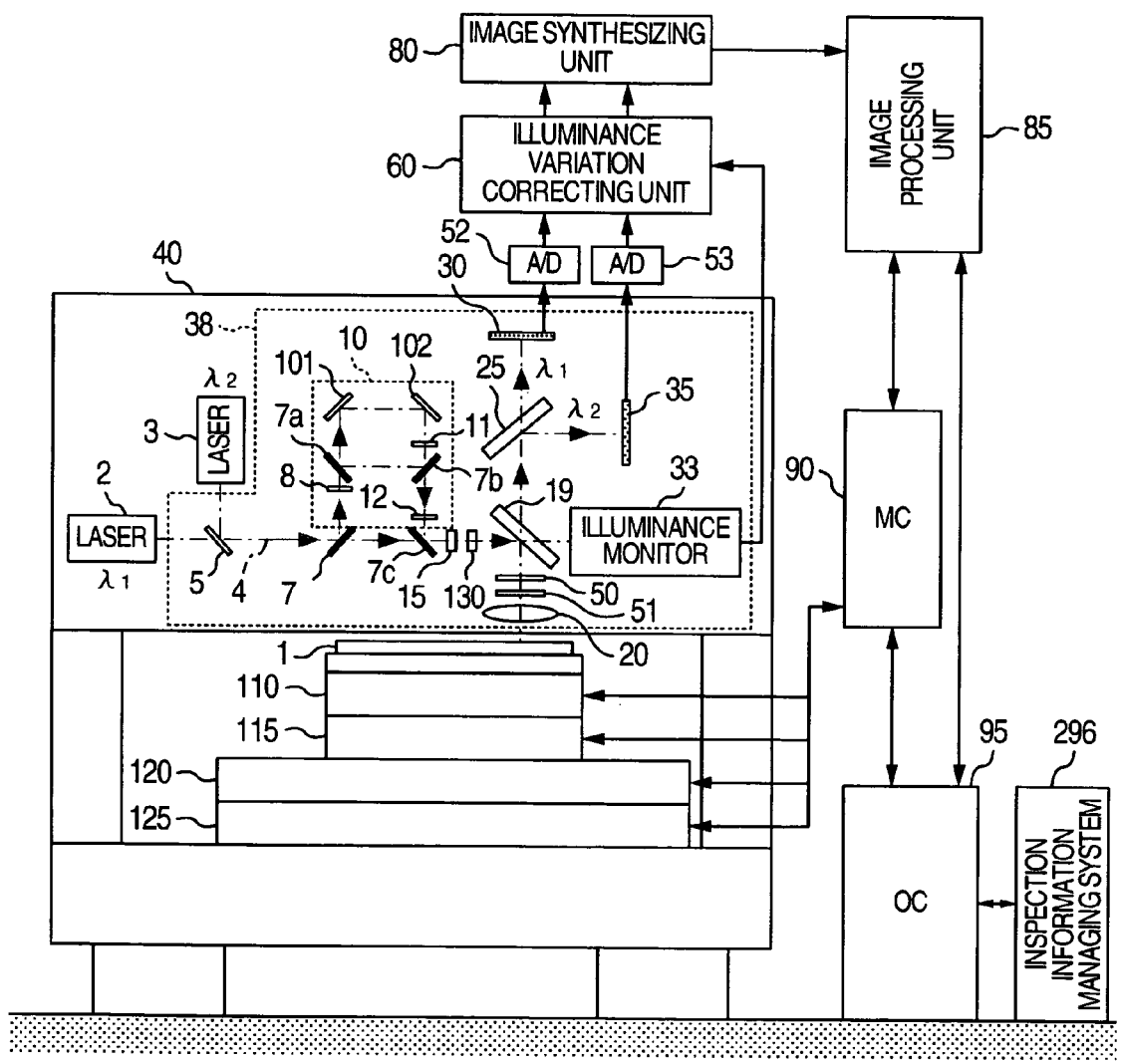
FIG. 1 is a schematic block diagram for indicating an entire arrangement of a defect inspecting apparatus according to the present invention.

One example of an embodiment mode of the present invention is shown in FIG. 1. Laser light emitted from a laser light source 2 and laser light having a wavelength different from that of the above laser light, emitted from another laser light source 3 are coaxially-processed by a dichroic mirror 8 so as to be formed as single laser light 4. This laser light 4 is entered into a polarizing beam splitter (will be referred to as a "PBS" hereinafter) 7 to be split into a P-polarized light component and an S-polarized light component. The P-polarized light component passes through this PBS 7. The S-polarized light component is reflected on the PBS 7 and then is projected therefrom, while an optical axis of this S-polarized light component is bent along a right angle direction. The S-polarized light component which is projected while bending the optical axis thereof along the right angle direction is entered into an optical path difference optical system 10. The light of the S-polarized light component which is entered into the optical path difference optical system 10 receives an optical path difference, and then is again coaxially-processed by a PBS 7c with the light which has been previously branched by the PBS 7. These plural sets of laser light pass through a spatial coherence reducing unit 15, and thereafter, penetrate through wavelength plates 50 and 51 having difference phase difference amounts and also an objective lens 20 to illuminate a wafer 1.

Among a plurality of light which have been reflected/diffracted/scattered on patterns formed on the wafer 1, such light propagated within an NA (Numerical Aperture) of the objective lens 20 is again captured by the objective lens 20, so that an optical image is focused on an image plane. It should be noted that in an image detecting optical path, while a dichroic mirror 25 is arranged which owns a similar branching characteristic to that of the above-described dichroic mirror 5 arranged in the illumination system, optical images formed in the respective wavelengths are detected by image sensors 30 and 35. This is because a nitre material of a lens is restricted in response to a wavelength of laser light, and chromatic aberration cannot be connected, so that the image sensors are arranged at focusing positions defined in response to the respective wavelengths of the laser light sources 2 and 3.

In accordance with the present invention, in order that very fine defects having dimensions of on the order of 20 to 30 nm can be detected which could be hardly detected in the conventional defect inspecting apparatus using the UV light (ultraviolet light: wavelength ($\lambda$)=about 365 nm), either DUV light (deep ultraviolet light: $\lambda$=approximately 300 to 180 nm) or VUV light (vacuum ultraviolet light: $\lambda$=approximately 180 to 100 nm; in case of F2 laser, $\lambda$=157 nm), which have shorter wavelengths than that of the UV light, may be employed as the illumination light source. Also, in the case that a laser is employed as the illumination light source, such a problem of interference of laser light will occur due to high coherence owned by the laser. In accordance with the present invention, in order to solve this problem, two-wavelength illumination is employed, so that temporal coherence is lowered.

Image signals which are detected by two systems of the image sensors 30 and 35 are converted by A/D converting circuits 52 and 53, respectively, into digital variable-density image data. In order normalize illuminance fluctuations sensed by an illuminance fluctuation monitor 33 of laser light, these digital variable-density image data are entered into an illuminance fluctuation correcting circuit 60, so that fluctuations in illumination light amounts may be normalized. The digital variable-density images, the illuminance of which has been corrected respectively, are inputted into an image synthesizing circuit 80 in order to synthesize a plurality of images with each other to produce a single image. The image synthesizing circuit 80 forms a synthesized image by electrically summing, for example, two images to each other. This synthesized image data is entered into an image processing unit 85 so as to perform a calculation by which a defect of the image may be extracted. It should also be noted that this defect inspecting apparatus may be arranged in another mode. That is, no image synthesizing operation is carried out in the image synthesizing circuit 80 in order that a defect may be inspected by employing such an image detected by any one of these two systems of the image sensors.

The defect information (namely, coordinate values and sizes of defects, classification results etc.) extracted by the image processing unit 85 is transferred to an operating computer 95 equipped with a display screen capable of displaying thereon defects. Also, information similar to this defect information is stored into an inspection information managing system 296. A $\theta$-stage 110, a Z-stage 115, an X-stage 120, and a Y-stage 125, which mount the wafer 1, are controlled by a mechanical control unit (MC) 90. Also, the operating computer 95 may operate the inspecting apparatus, and issues an instruction to the mechanical control unit 90 in the case that this operating computer 95 executes operations of a mechanism unit. Further, the operating computer 95 may interface with an operator, for example, setting of inspection conditions.

Also, in accordance with the present invention, a light source operable in the VUV range is mounted. As a result, in order to minimize an attenuation of light within an optical path, such a region 38 is purged which contains optical paths defined by that the laser light emitted from the laser light source 2 and the laser light emitted from the laser light source 3 are reached to the image sensors 30 and 35, respectively. It should also be noted that a working distance between the objective lens 30 and the wafer 1 is set to an atmospheric environment. As a consequence, the wafer 1 may be handled under atmospheric environment, so that cost of the defect inspecting apparatus can be reduced, and also, the wafer transportability thereof can be improved.

Also, in accordance with this embodiment mode, the description has been made by employing the laser light sources. Alternatively, these laser light sources may be readily replaced by lamp light sources. Alternatively, since such illumination light having a wavelength shorter than, or equal to 200 nm is employed, resolution may be improved and very fine defects having dimensions of approximately 30 to 20 nm may be detected.

The optical path difference optical system 10 will now be explained with reference to FIG. 1 and FIGS. 2A and 2B. The laser light which has been emitted from the laser light sources 2 and 3 having the different wavelengths and has been coaxially-processed by the dichroic mirror 8 is split into the transmission light (P-polarized light) and the reflection light (S-polarized light) by the PBS 7. The S-polarized light component reflected by the PBS 7 is conducted to the optical path difference optical system 10. Since this S-polarized light passes through a ½-wavelength plate 8, such a phase difference is given to in such a manner that this S-polarized light may become P-polarized light with respect to the PBS 7a of a circulating optical path which is formed by the PBS 7a, the PBS 7b, a total reflection mirror 101, and another total reflection mirror 102, and then, penetrates through the PBS 7a.

The penetrated light is reflected by both the total reflection mirrors 101 and 102, and then passes through a ½-wavelength plate 11, so that such a phase difference is given in such a manner that a P-polarized light component may be equivalent to an S-polarized light component with respect to the PBS 7b provided on the output side of the circulating optical path. As a result, as to such a light which is entered into the PBS 7b provided on the output side of the circulating optical path, the S-polarized light component is reflected to the side of the PBS 7a, and then is again entered into the circulating optical path. In contrast to this S-polarized light component, the P-polarized light component penetrates through the PBS 7b and then is entered into a ½-wavelength plate 12, and such a phase difference is given in such a manner that this P-polarized light becomes S-polarized light with respect to the PBS 7a, and thereafter, is entered into the PBS 7c. The S-polarized light which has been reflected by this PBS 7 and has been entered into the PBS 7c after being penetrated via the circulating optical path is coaxially-processed with such a P-polarized light which has passes through the PBS 7 and then has been entered into the PBS 7c, so that the coaxially-processed polarized light may become illumination light for illuminating an object 1.

It should also be understood that within the circulating optical path, the splitting operation between the reflection and the transmission is repeatedly performed in the PBS 7b in the second circulating time and succeeding circulating times, and the reflected S-polarized light is furthermore repeatedly circulated. This is shown in a Table shown in FIG. 2B. In addition, a difference between an optical path length of S-polarized light which is reflected by the PBS 7 and is entered via the circulating optical path into the PBS 7c and an optical path length of P-polarized light which passes through the PBS 7 and is directly entered into the PBS 7c may have such a distance which is longer than, or equal to the below-mentioned coherent distance of the laser light 4, and the temporal coherence of the light which has been coaxially-processed by the PBS 7c may be reduced. It should also be noted that a formula capable of calculating a coherent distance "L" is indicated in an expression (1):

$$L = \frac{\lambda c^2}{\Delta \lambda} \quad \text{(expression 1)}$$

The coherent distance "L" is directly proportional to a square of a central wavelength "λc" of illumination light, and is inverse-proportion to a wavelength width of the illumination light. For instance, a coherent distance "L" in the case that an F2 laser (λ=157 nm) for generating vacuum ultraviolet light (VUV light) is employed as the illumination light source is equal to several tens of nm.

In this case, FIG. 3 shows an example of a calculation of a splitting ratio by the PBS 7 for splitting the incident laser light into the P-polarized light and the S-polarized light. The P-polarized light component of the laser light 4 which is entered into the PBS 7 penetrates through the PBS 7, and the S-polarized light component thereof is reflected. As a result, in the case that the entered laser light 4 corresponds to linearly polarized light having a vibration plane at an angle of "θ" with respect to the vibration direction of the P-polarized light, a light amount of transmitting polarized light may be obtained based upon the following expression (2):

$$T = \frac{(\cos\theta)^2}{(\cos\theta)^2 + (\sin\theta)^2} \quad \text{(expression 2)}$$

Figure 4:
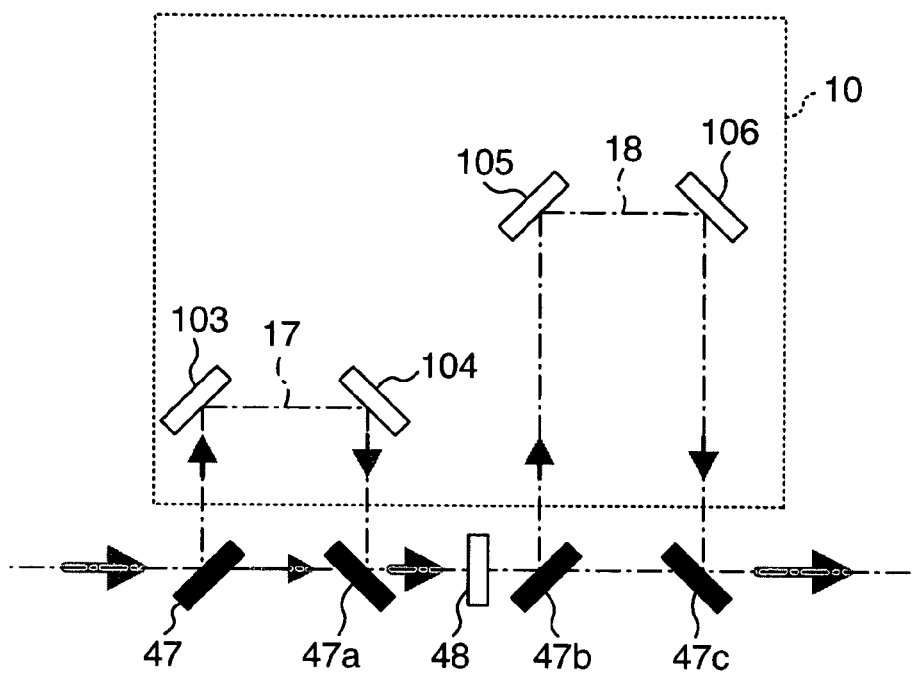
FIG. 4 is a front view for representing an optical path difference optical system according to another embodiment of the present invention.

FIG. 4 shows an example of an optical path difference optical system 10' established based upon another method. In the case of FIG. 4, such a structure that the laser light 4 is entered into the PBS 47 and then the S-polarized light component is reflected and the P-polarized light component passes through the PBS 47 is identical to the structure explained in FIG. 1 and FIG. 2. In the structure of FIG. 4, the S-polarized light component of the laser light 4 which is reflected on the PBS 47 is projected to the side of a first optical path difference optical system 17. This first optical path difference optical system 17 is constituted by two sheets of total reflection mirrors 103 and 104. In such a structure, the S-polarized light which is entered in the first optical path difference optical system 17 is reflected by two sheets of these total reflection mirrors 103 and 104, and is entered into the PBS 47, and then is again coaxially-processed with the P-polarized light which passes through the PBS 47. In this case, an optical path length of the first optical path difference optical system 17 has a difference longer than, or equal to the coherent distance with respect to an optical path length of the P-polarized light which passes through the PBS 47 and is directly entered into the PBS 47a.

Since the light which is synthesized by the PBS 47a penetrates through a ¼-wavelength plate 48, this light is converted into circularly polarized light. The circularly polarized light is entered into the PBS 47b so as to be again split into a P-polarized light component and an S-polarized light component. This S-polarized light component is entered into a second light path different optical system 18. The S-polarized light which is entered into this second optical path difference optical system 18 is reflected by two sheets of total reflection mirrors 105 and 106, then is entered into the PBS 47c so as to be again synthesized with the P-polarized light component which has passed through the PBS 47b.

An optical path length of this second optical difference optical system 18 is longer than the above-described optical path length of the first optical path difference optical system 17 by such a distance equivalent to the coherent distance of the laser light 4.

In this case, the S-polarized light which will be entered into the second optical path difference optical system 18 corresponds to such light which is split from the circularly polarized light converted by causing both the P-polarized light component and the S-polarized light component which have been synthesized with each other by the PBS 47a to pass through the ¼-wavelength plate 48. As a result, an amplitude of this S-polarized light becomes a half of an amplitude of each of the light (S-polarized light component) which has penetrated through the first optical path difference optical system 17, and the light (P-polarized light component) which has not passed through this first optical path difference optical system 17.

In this case, it is so assumed that a difference between the optical path length of the S-polarized light which passes through the first optical path difference optical system 17 and the optical path length of the P-polarized light which does not pass through the first optical path difference optical system 17 but is directly reached from the PBS 47 to the PBS 47a is equal to "L1", whereas a difference between the optical path length of the S-polarized light which passes through the second optical path difference optical system 18 and the optical path length of the P-polarized light which does not pass through the second optical path difference optical system 18 but is directly reached from the PBS 47b to the PBS 47c is equal to "L2". In this case, four systems of rays are formed by the first optical path difference optical system 17 and the second optical path difference optical system 18. Differences among optical path lengths of these rays are longer than the coherent distance, respectively. These rays are: (1) a ray (optical path difference 0) which does not pass through an optical path length of two systems;

(2) a ray (optical path difference L1) which has passed through only the first optical path difference optical system; (3) a ray (optical path difference L2) which has penetrated through only the second optical path difference optical system; and (4) a ray (optical path difference L1+L2) which has passed through both the first and second optical path difference optical systems. An amplitude of each of these four systems of rays is, in principle, equal to each other. However, in an actual case, there is more, or less a difference among these amplitudes in such a case, this balance may be adjusted based upon setting condition of the ¼-wavelength plate.

As previously explained, since the four systems of such light having the large optical path differences are employed as the illumination light, the adverse influence of the interference caused by the stray light (namely, such light which is unnecessarily reflected on optical components, and is not reached to wafer, but is directly reached to image sensors) appearing on the image sensors 30 and 35 can be reduced. As a result, levels of the noise can be lowered, and levels of threshold values of the defect inspection can be suppressed to low levels, so that the defect inspection can be realized in high sensitivities.

Furthermore, in FIG. 1 and FIGS. 2A and 2B, the embodiment with employment of the ½-wavelength plate has been described. Also, in FIG. 4, the embodiment with employment of the ¼-wavelength plate has been explained. A similar effect may be achieved even when any one of these wavelength plates is employed, depending upon setting methods of these wavelength plates. As a consequence, the arrangements shown in FIG. 2 and FIG. 4 merely constitute one example, and therefore, various applications thereof may be conceived.

Figure 5:
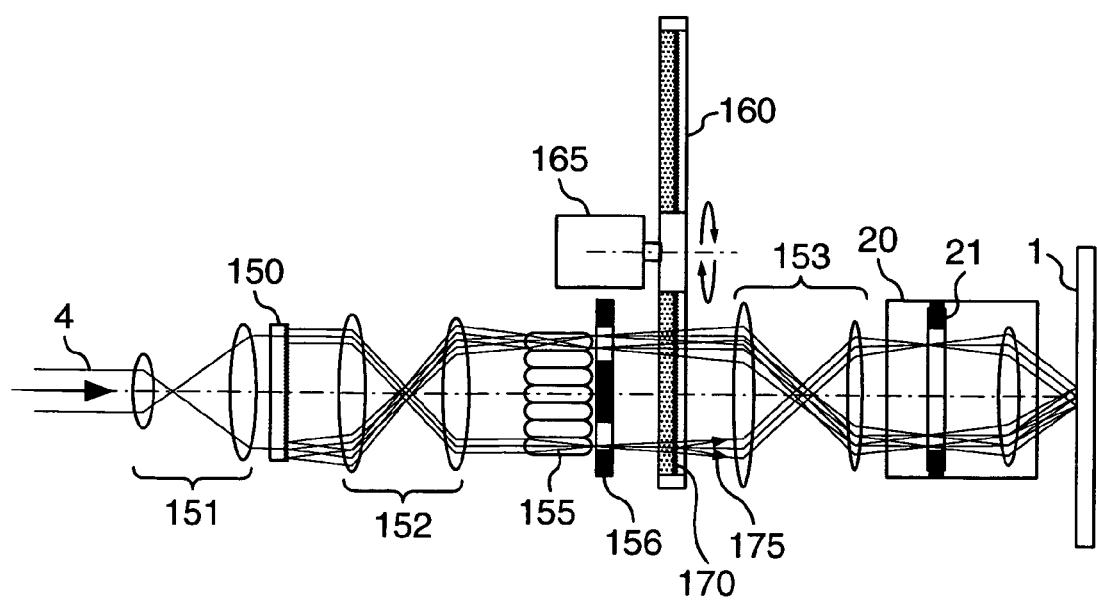
FIG. 5 is a schematic block diagram for indicating an arrangement of an illumination optical system capable of reducing coherence.

Referring now to FIG. 5, a detailed description is made of the spatial coherence reducing unit 15 of the laser light. The laser light 4 which has passed through either the optical path difference optical system 10 or the optical path difference optical system 10' is entered into a beam expander 151 so as to expand a beam diameter thereof, and thereafter, is entered into a first diffusing plate 150, so that the directivity of the laser light 4 is diffused.

Next, this diffused light passes through a first lens system 152, and thereafter is entered into a fly eye lens 155 which is constructed of a rod lens. A point light source group is formed at a projection end of the fly eye lens 155 in response to a diffusing degree of the fist diffusing plate 150, and this point light source group constitutes a secondary light source. Light emitted from the secondary light source is entered into a second diffusing plate 160. This second diffusing plate 160 is constructed in a rotatable manner, and is rotary-driven by a motor 165. When the second diffusing plate 160 is rotated by the motor 165, since a phase of light which is entered into the second diffusing plate 160 is temporally disturbed, a coherence may be reduced. The light which has passed through this second diffusing plate 160 forms a secondary light source image at a position of a projecting pupil 21 of the objective lens 20 by way of a second lens system 153. As a result, this may construct such a Koehler illumination in which an illuminance distribution becomes uniform on an object plane. It should be noted that the temporal/spatial coherence of the laser light can be reduced by combining the previously-indicated optical path difference optical systems, the first and second diffusing plates, and furthermore the fly eye lens 155 with each other.

Figure 6A:
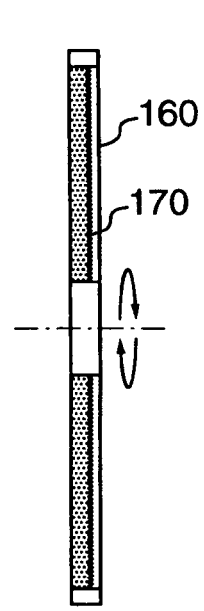
FIG. 6A is a side view of a rotary diffusing plate.
Figure 6B:
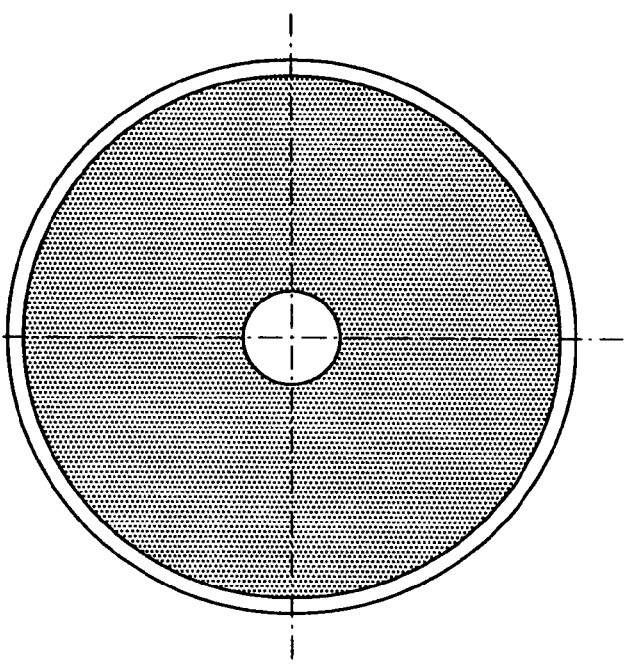
FIG. 6B is a front view of the rotary diffusing plate.

In this case, FIGS. 6A and 6B represent an example of a structure of the second diffusing plate 160. The diffusing plate 160 is arranged in a doughnut shape. This diffusing plate is rotated by the motor 165, so that a phase of illumination light may be temporally distributed. A rotation period of this diffusing plate 160 may be desirably synchronized with a time period in which an image is acquired. For instance, in the case that an image acquisition time period is selected to be "T1", the rotation period of the diffusing plate 160 is set to T1/n. In this formula, symbol "n" is a natural number.

Figure 7:
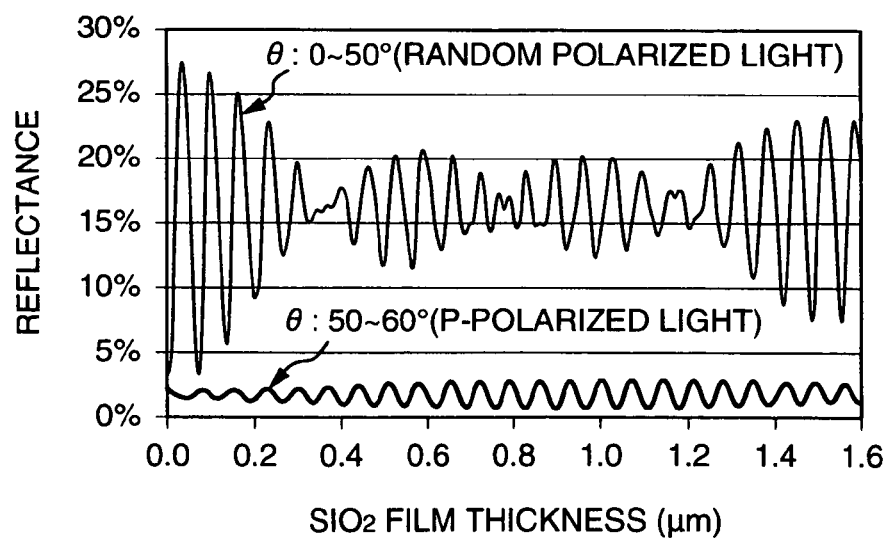
FIG. 7 is a graphic representation for showing a relationship between a film thickness of $SiO_2$ and reflectance.

FIG. 7 represents a relationship between a film thickness of a model and reflectance of this model in which an electric insulating film is formed on surface of the wafer 1. As to the insulating film, $SiO_2$ is employed as the model. It should be noted that the illumination light is monochromatic color having a wavelength of 193 nm, and incident light was calculated as to two sorts of illumination of 0 to 50°, and illumination of 50 to 60° which becomes near the Brewster angle (57.5°). Also, refractive indexes of the insulating film and $SiO_2$ correspond to that of the wavelength of 193 nm.

In the illumination of 0 to 50° (random polarized light), reflectance thereof is vibrated in connection with an increase in film thicknesses. This is caused by thin-film interference. When the film thickness is changed, an optical path difference between light reflected on the surface of the insulating film and light which is entered into the thin film and is derived therefrom into an atmosphere is changed, the reflectance is vibrated by way of the change in the film thicknesses. This vibration is fluctuated within a width of 3% to 28% as to the reflectance, namely, there are 25% of vibration widths. This reflectance variation indicates brightness of an optical image formed on an image plane. As a consequence, in such a case that patterns formed on the wafer 1 are compared with each other for an inspection purpose, if film thicknesses of insulating films are different from each other in two regions for comparisons, then a brightness difference is increased. In the case that this film thickness variation of the insulating films does not own the fatal characteristic with respect to a device, this brightness fluctuation constitutes noise while defects are detected.

Conversely, in the case that the film thickness variation own the fatal characteristic as to a device, since this film thickness variation is required to be detected, if a variation of reflectance with respect to the film thickness is large, then this film thickness variation may be easily detected. However, in an example of a semiconductor manufacturing step, since this film thickness variation does not own the fatal characteristic as to a device, if a vibration width of reflectance is large in response to a film thickness of an insulating film, then this film thickness variation may constitute noise in view of inspection sensitivity. As a method for reducing this reflectance variation width, Brewster angle illumination has been employed in accordance with the present invention. This Brewster angle illumination implies such an illumination that when P-polarized light is illuminated at a specific angle, this P-polarized light is not reflected on a boundary between an insulating film and air, but the entire P-polarized light may penetrate therethrough. As a result, amplitude splitting does not occur which causes thin-film interference, but there is no reflectance variation in connection with film thickness variations. In FIG. 7, a calculation result in the case that the P-polarized light is illuminated at an incident angle of 50° to 60° is also indicated.

In this illumination in the vicinity of this Brewster angle, a variation of reflectance may be reduced to approximately 0.5% to 3%. As a consequence, the P-polarized light is illuminated at an incident angle in the vicinity of the Brewster angle, so that brightness fluctuations occurred in connection with the film thickness variations of the insulating film can be reduced. As a result, since the noise produced in the inspection may be reduced, the defect detecting sensitivity may be improved. Next, a description will now be made of an example for illuminating light at the Brewster angle with reference to FIG. 5. An incident antle of illumination light may be determined based upon a shape of a secondary light source image which is formed at a position of a pupil 21 of the objective lens 20

To illuminate light at an angle in the vicinity of an incident angle 57° which constitutes the Brewster angle, a secondary light source image having a ring shape is required to be imaged at the position of the pupil 21. As a consequence, since an aperture stop 156 having a ring shape is arranged in the vicinity of the projection edge of the fly eye lens 155, the light can be illuminated at such an incident angle in the vicinity of the Brewster angle. It should also be noted that this aperture stop 156 may be arranged at any other positions than the projection edge of the fly eye lens 155, namely, at a position in the vicinity of a conjugate position in such a case that this conjugate position is present with respect to the projection pupil 21 of the objective lens 20. Also, only such a light which is reflected/diffracted/scattered at an angle of approximately 57° with respect to the optical axis is reached to an image sensor, so that fluctuations in reflectance which are caused by the thin-film interference can be reduced. This alternative case is realized as follows: That is, while a spatial filter (not shown) is arranged at either the position of the pupil 21 of the objective lens 20 or the position on the side of the conjugate image (on the side of image sensor), only such light which is reflected/diffracted/scattered at near the incident angle of 57° with respect to the optical axis is caused to be reached to the image sensor among the light which has been reflected/diffracted/scattered on the wafer 1 (detection of Brewster angle). In case of this Brewster angle detecting the incident angle of the illumination light need not be limited only to the Brewster angle.

While both the Brewster angle illumination and the Brewster angle detecting methods have been described. Alternatively, the Brewster angle illumination may be readily combined with the Brewster angle detecting system. Also, as to the aperture stop 156 and the spatial filter, other aperture stops/spatial filters having different shapes may be installed, based upon such a fact as to whether or not the wafer 1 has the insulating film.

Figure 8:
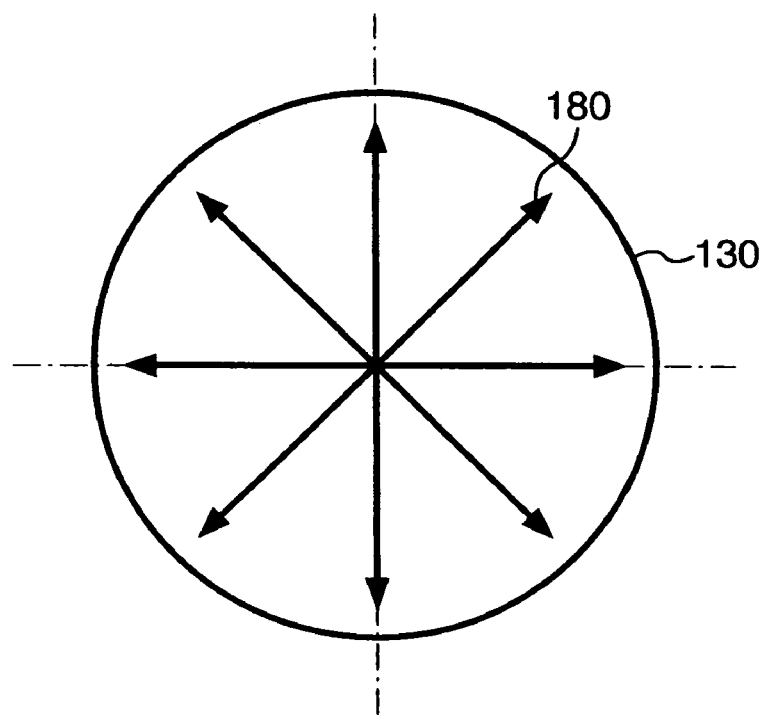
FIG. 8 is a front view for indicating a radiation polarizer.

Next, with respect to a measure capable of illuminating P-polarized light, an example with employment of a radial-shaped polarizer will now be explained with reference to FIG. 8.

Figure 9:
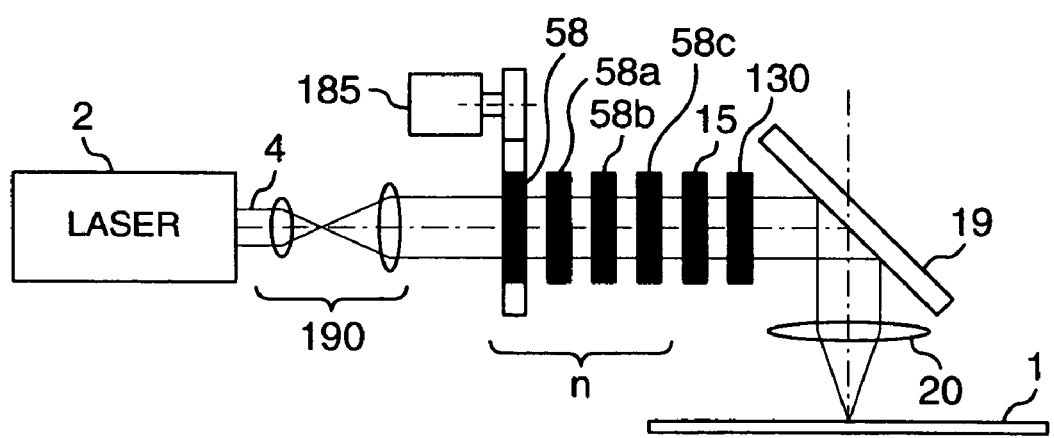
FIG. 9 is a schematic block diagram for representing an arrangement of an optical system for correcting deviation of illumination light along a vibration direction thereof.

Although laser light emitted from a light source is linearly polarized light, the polarized light is disturbed by a first diffusing plate and a second diffusing plate, and the like. As a result, in order to illuminate the wafer 1 by P-polarized light, the polarized light must be vibrated in a radial form at the projection pupil plane 21 of the objective lens, while the optical axis is set as a center. As this measure, a filter (radial-shaped polarizer) 130 is provided at such a conjugate position with respect to the pupil position 21 of the objective lens 20, so that the P-polarized light can be illuminated on the wafer 1. This filter 130 may penetrate therethrough illumination light along the radial direction as to the vibration direction of the illumination light, while the optical axis is positioned at a center. It should also be understood that even when this filter 130 is located at the pupil position 21 of the objective lens 20, or in an illumination optical path located other than the conjugate position of this pupil position 21, otherwise, in a detection optical path, an advantageous effect may be achieved. Also, in a case that both the first and second diffusing plates are not arranged in the illumination system, and also in such a case that deviation is still left along the vibration direction even: after the illumination light has passed through the diffusing plates, even if the above-described filter 130 is arranged, uniform polarized-light illumination cannot be realized. As a consequence, a method for eliminating deviation along the vibration direction is shown in FIG. 9. It should also be noted that a diffusing plate is not illustrated in this example.

A beam diameter of the linearly polarized light 4 emitted from the laser light source 2 is expanded by a beam expander 190. The expanded linearly polarized light is entered into a ½-wavelength plate 58, and thus, the polarized light is rotated at a speed 4 times higher than the rotation frequency of this ½-wavelength plate 58 and then, the rotated polarized light is projected therefrom. It should also be noted that this ½-wavelength plate 58 is rotary-driven by a motor 185.

The light which has penetrated through the ½-wavelength plate 58 furthermore passes through ½-wavelength plates 58$a$, 58$b$, and 58$c$. At this time, every time this light penetrates through the respective ½-wavelength plates 58$a$, 58$b$, 58$c$, a rotation speed of a vibration plane becomes 4 times. It should also be noted that although the ½-wavelength plates 58$a$, 58$b$, 58$c$ are fixed in this example, these ½-wavelength plates 58$a$, 58$b$, and 58$c$ may be rotated in a similar to the ½-wavelength plate 58. The light which has passed through these ½-wavelength plates 58, 58$a$, 58$b$, and 58$c$ becomes rotary polarized illumination light, and then is reflected on a beam splitter 19. The reflected illumination light is entered into an objective lens 20 so as to be illuminated on the wafer 1. It should also be noted that in order to illuminate the wafer 1 by the P-polarized light by employing the rotary polarized illumination light, the radial-shaped polarizer 130 shown in FIG. 8 is arranged between the spatial coherence reducing unit 15 and the beam splitter 19 as indicated in FIG. 9. It should also be understood that as an arrangement for arranging the radial-shaped polarizer 130 in the detection optical path, this radial-shaped polarizer 130 may be arranged between the beam splitter 19 and the image sensor 30.

Also, as the illumination method for not causing the thin-film interference, there is a total reflection angle illuminating method for totally reflecting illumination light on a surface of a substrate. A formula (expression 3) for calculating a total reflection angle "θc" used to totally reflect illumination light on a substrate is given as follows:

$$\sin \theta c = n2/n1 \quad \text{(expression 3).}$$

In this formula, symbol "n1" shows a reflective index within air, and symbol "n2" represents a reflective index of an insulating film.

Figure 10:
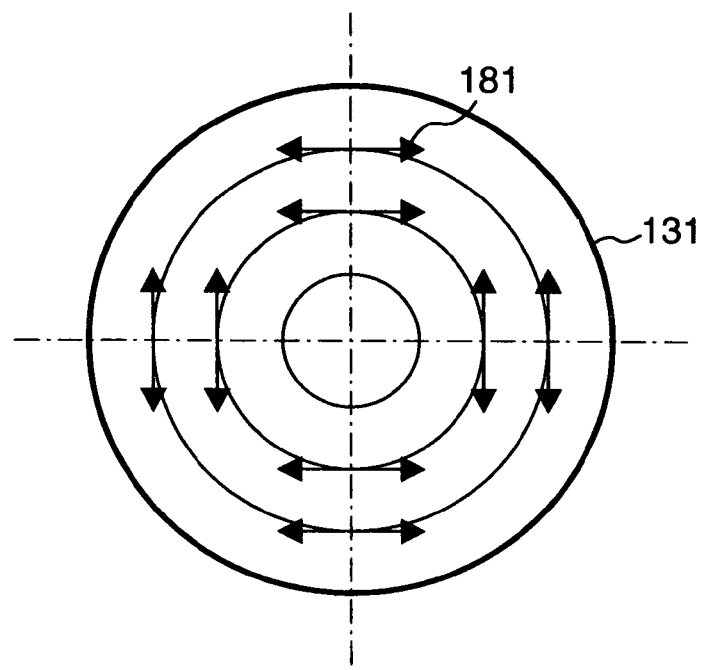
FIG. 10 is a front view for indicating a polarizer.

In order to realize the total reflection illumination, an incident angle must be set to 90 degrees. It is practically difficult to realize this setting of the incident angle in view of a structure. As a consequence, in order to increase reflectance on a surface of an insulating film, while the incident angle is increased as large as possible (namely, is approximated to 90 degrees), the surface of the insulating film must be illuminated by using S-polarized light. To realize the S-polarized light illumination, the vibration direction of the illumination light must be set to a circumferential direction on the plane of the pupil 21 of the objective lens 20, while the optical axis is set as a center. To realize this condition, such a polarizer 131 having a characteristic shown in FIG. 10 may be arranged on the illumination optical path. Also, the description has been made of such a fact that both the polarizers 130 and 131 shown in FIG. 8 and FIG. 10 are arranged in the illumination optical path. Alternatively, even when an analyzer (not shown) having a similar characteristic is arranged in the detection system, an equivalent effect may be achieved. In this example, the TTL (Through The Lens) system for illuminating the illumination light through the objective lens 20 has been explained. Alternatively, a darkfield illumination system for illuminating illumination light from an outer side of an objective lens may be conceived. This darkfield illumination system is referred to as "off-axis illumination."

Figure 11:
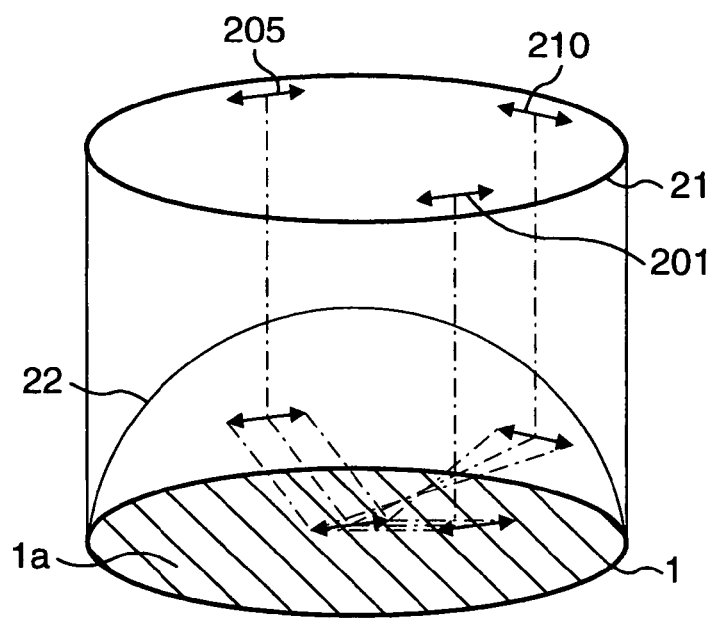
FIG. 11 is a schematic diagram for schematically showing polarization conditions of both zero-order light and high-order diffraction light at a surface of a wafer and a pupil plane of an objective lens.

FIG. 11 shows polarized light by illumination light, polarized light of direct reflection light or regular reflection light (zero-order light), and polarized light of high-order diffraction light. It is so assumed that polarized light 201 of illumination light is vibrated along a circumferential direction at the pupil plane 21. This light illuminates a pattern formed on the wafer 1. It should also be understood that a semi-spherical portion 22 on the wafer 1 schematically indicates conditions of diffraction by the objective lens 20. The zero-order light which is directly reflected on the wafer 1 is propagated to a position which is symmetrical to the optical axis at the pupil position 21. At this time, the polarized light owns a vibration plane along the same circumferential direction to that of the illumination light. In contrast, the diffraction directions of the high-order diffraction light are different from each other in response to a direction of a pattern formed on the wafer 1. As a result, since the direction along which the high-order diffraction light is made different with respect to the illumination light, a vibration direction 210 of the high-order diffraction light at the pupil plane 21 becomes a different vibration plane with respect to the vibration direction 201 of the illumination light and the vibration direction 205 of the zero-order light. It should also be noted that the polarized light with respect to the wafer 1 is identical to the illumination light, the zero-order light, and the high-order diffraction light, and is stored. This is schematically indicated in FIG. 12.

Figure 12:
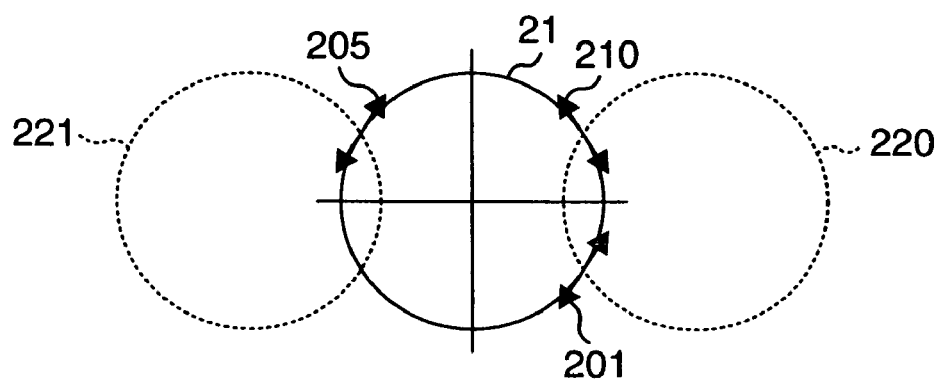
FIG. 12 is a schematic diagram for schematically showing polarization conditions of both zero-order light and high-order diffraction light at a surface of a pupil plane of an objective lens.

In FIG. 12, a vibration direction of illumination light at the pupil plane 21 of the objective lens 20 is indicated by 201. A distribution of +1-order light is represented by 220, which is produced by a pattern on the wafer 1. Also, a distribution of −1-order light is denoted by 221. In this case, among reflection light reflected from the wafer 1, which is caused by the illumination light having the vibration direction 201 at the pupil plane 21, the zero-order light which has been again captured by the objective lens 20 is reached to a position 205. On the other hand, the +1-order diffraction light is reached to 210. At this time, the vibration direction at the pupil plane as to the zero-order light is different from the vibration direction at the pupil plane as to the high-order diffraction light (note that vibration directions thereof are identical to each other with respect to wafer). As a result, in the case that the polarized light is illuminated, since a polarization filter which may penetrate therethrough a large amount of the +1-order diffraction light is arranged in the detection optical path, the zero-order light may be suppressed and also the high-order diffraction light containing the +1-order diffraction light can be effectively penetrated. Since this high-order diffraction light contains a larger amount of pattern information than that of the zero-order light, contrast of an optical image can be increased by effectively detecting the high-order diffraction light. Otherwise, the contrast of the optical image may be adjusted to desirable contrast.

Figure 13:
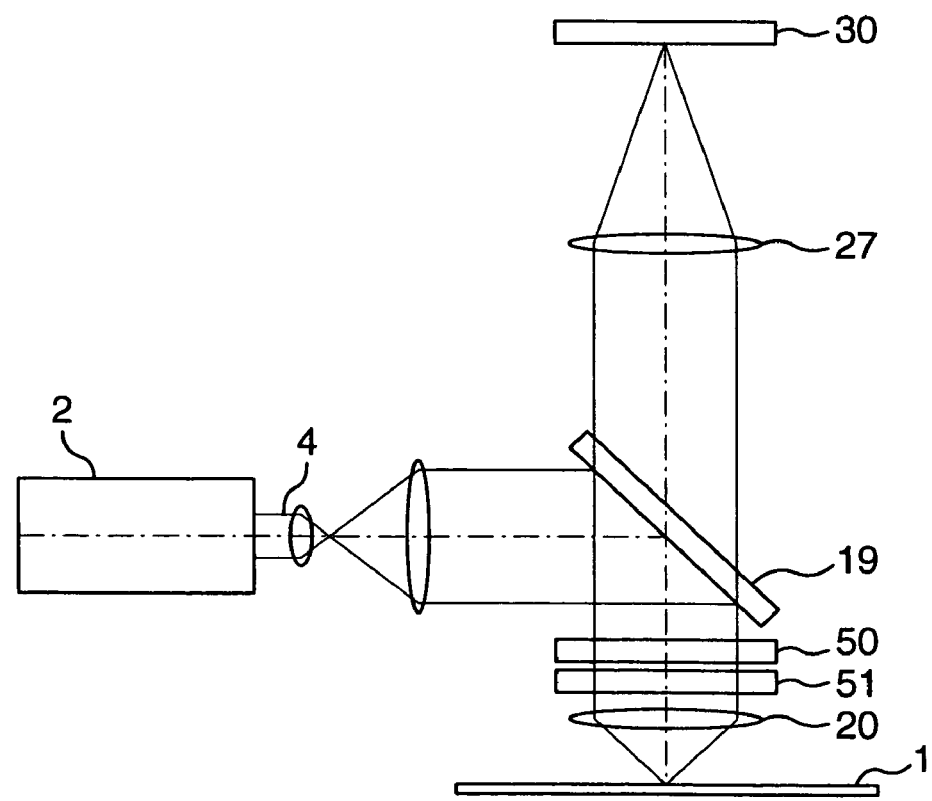
FIG. 13 is a schematic block diagram for indicating an arrangement of an optical system for controlling amplitudes of the zero-order light and of the high-order diffraction light.

FIG. 13 shows an example of realizing this contrast adjustment. As to the linearly polarized light emitted from the laser light source 2, the S-polarized light thereof is reflected on the PBS 19 to constitute such an illumination light which is directed to the side of the wafer 1. This illumination light may become such an elliptically polarized light having a desirable ellipticity and an azimuth angle of an ellipse by that the azimuth angle of the ellipse is adjusted by a ½-wavelength plate 50 and the ellipticity is adjusted by a ¼-wavelength plate 51. This illumination light is illuminated via the objective angle 20 onto the wafer 1. The light which has been reflected/diffracted/scattered on the wafer 1 is again captured by the objective lens 20, and passes through the ½-wavelength plate 50 and the ¼-wavelength plate 51, and then is entered into the PBS 19. A ratio of zero-order light passing through the PBS 19 to the light entered into this PBS 19 may be substantially determined based upon the ellipticity of the illumination adjusted by the ¼-wavelength plate 51. In other words, when the ¼-wavelength plate is adjusted so as to make the ellipticity of illumination flat (namely, ellipticity is approximated to zero), a ratio of zero-order light which passes through the image sensors 30 and 35 is lowered.

In contrast, a ratio of high-order diffraction light (±1-order diffraction light and like) which is reached to the image sensors 30 and 35 is different in response to directivity of a pattern. As a consequence, since both the ½-wavelength plate 50 and the ¼-wavelength plate 51 are adjusted so as to properly set both the ellipticity and the azimuth angle of the ellipse, amplitudes of the zero-order light and of the high-order diffraction light which are reached to both the image sensors 30 and 35 can be adjusted, so that the contrasts of the optical images formed on the image sensors 30 and 35 can be adjusted. As a consequence, it is possible to form such an optical image capable of advantageously detecting defects, and thus, an improvement in the inspection sensitivity can be realized.

FIG. 14 indicates an example of images which were detected by employing this optical system. FIG. 14A indicates that an image of the wafer 1 was detected by using the normal microscope, and FIG. 14B represents that the image of the wafer 1 was detected by employing the optical system of the present invention. In FIG. 14A, lines an spaces, which are wired along a lateral direction, cannot be separated from each other, so that shape failures of the wiring lines cannot be inspected. In contrast, in the image of FIG. 14B detected according to the present invention, since the lines and the spaces are separated in higher contrast, it can been understood that the inspection of the line and space can be carried out in a higher sensitivity.

Also, FIG. 15 represents images of rear-sided focal positions (pupil positions: Fourier transforming plane) of the objective lens 20 when lines and spaces which were formed along a longitudinal direction were detected. FIG. 15A shows a pupil image of the normal illumination, and FIG. 15B indicates a pupil image obtained when the optical system of the present invention was employed. In FIG. 15A, optical strengths (brightness) of zero-order light distributed over the entire pupil are substantially equal to optical strengths (brightness) of ±1-order diffraction light distributed at right/left peripheral portions of the pupil. In contrast, as shown in FIG. 15B, in the case that the optical system according to the present invention is employed, the ±1-order diffraction light can be detected by emphasizing the ±1-order diffraction light. As a result, it can be understood that the very finer pattern shapes can be restored into the optical images. As a consequence, in accordance with the present invention, very finer pattern defects can be detected, as compared with that of such a case that the normal optical system is employed.

Next, a method for adjusting pattern contrast of an optical image by employing the optical system according to the present invention is illustrated in FIG. 16. An abscissa of this drawing indicates a ratio of zero-order light which has been direct-reflected on the wafer 1 penetrates through the PBS 19, whereas an ordinate thereof represents pattern contrast on an image plane. Since transmittance of the zero-order light is converted, a ratio of the zero-order light to the high-order diffraction light on the image plane can be controlled, so that the pattern contrast is changed.

In general, in order to improve contrast of an optical image, an amplitude of zero-order light is made substantially equal to an amplitude of high-order diffraction light. It should be noted that since this contrast corresponds to a difference between brightness of a pattern portion and brightness of a space portion which constitutes a background of this pattern portion, this contrast may be influenced by reflectance of the background and reflectance of the pattern portion. Also, a ratio of the zero-order light to the high-order diffraction light may be influenced by a frequency and a material of a pattern, an azimuth angle of polarized light of illumination light, NA (Numerical Aperture) of an objective lens, and the like. However, since the amplitude of the zero-order light and the amplitude of the high-order diffraction light are controlled, the pattern contrast can be adjusted under desirable condition. It should also be noted that in order to adjust the contrast, both the azimuth angle of the elliptically polarized light and the ellipticity must be adjusted, and therefore, both the ½-wavelength plate 50 and the ¼-wavelength plate 51 must be constructed in a rotatable manner (electrically rotatable).

Next, FIG. 17 shows effects of improvements in inspection sensitivities in the case that the optical system of the present invention is employed. For instance, it is so assumed that such a pattern indicated in FIG. 17A has been formed on the wafer 1 which is directed for inspection. It should be noted that the pattern of FIG. 17A schematically indicates one die 280 formed on the wafer 1. Within this pattern, there are a region 282 where a pattern pitch is coarse, a region 286 where a pattern pitch is fine, and a region 284 where a pattern pitch is medium. In this case, FIG. 17B shows such an example that these images were detected by using the normal optical system. FIG. 17B represents an optical strength distribution, taken along a line A—A sown in FIG. 17A. In the region where the pattern pitch is coarse (namely, region where pattern frequency is low), sufficiently high contrast can be obtained. However, when the pattern pitch becomes fine (when pattern frequency becomes high), the pattern contrast is lowered.

In defect inspection, the finer a pattern pitch is, the higher the fatality due to defects becomes. Although the region where the pattern pitch is fine is wanted to be detected in view of the defect inspection, the normal optical system cannot realize this defect detection. In contrast, in the case that the optical system according to the present invention is employed, the amplitude ratio of the zero-order light to the high-order diffraction light can be adjusted, and as represented in FIG. 17C, while the pattern contrast of the region where the pattern pitch is coarse is maintained, the pattern contrast of the region where the pattern pitch is fine can be increased. As a result, since the optical image with the high contrast can be obtained even when the fine pattern portion having the high totality is inspected, the defects can be inspected under such a condition that the inspection sensitivity is maintained in a high sensitivity.

Also, in accordance with the present invention, in the case that the region where the pattern pitch is coarse is inspected, both the ½-wavelength plate 50 and the ¼-wavelength plate 51 are adjusted so as to make the contrast equivalent to that of the normal illumination, the image can be detected without lowering the inspection sensitivity.

Next, a method for correcting illuminance fluctuations of laser light is indicated in FIG. 18. For example, in the case that a laser light source is a pulse oscillation, if there are strength fluctuations in the respective pulses, then illuminance fluctuations will be temporally produced on the wafer 1. There is such a trend that when a pulse oscillating frequency is increased, this illuminance fluctuation becomes conspicuous. As a consequence, in order to execute inspection in a high speed, this problem of the illuminance fluctuation cannot be neglected.

Assuming now that the pulse frequency is constant, when an inspection speed is increased, a total number of pulses is decreased which are illuminated so as to photograph one pixel of an image. As a result, when strength variations are produced in the respective pulses of illumination, brightness of detected images is different from each other. This brightness difference cannot be discriminated from a difference in reflectances of patterns at a glance, resulting in noise during inspection. To correct this illuminance fluctuation, illuminance of illumination must be monitored.

An arrangement shown in FIG. 18 is such an arrangement that while the wafer 1 is scanned in a constant speed along an X direction, an image is detected by using a one-dimensional image sensor. For instance, such a light which does not constitute the illumination light of the wafer 1 among laser light emitted from a laser light source is entered into a light amount monitor 55. Then, a light amount detected by this light amount monitor 55 is inputted into an image illuminance correcting circuit. Also, into this image illuminance correcting circuit, a digital image is entered, and this digital image is produced by A/D-converting an image detected by the image sensor 30. Assuming now that illuminance when the image is detected is Iref(t) and brightness of the image is I(t, y), a light amount of each of pixels is corrected (Ical) based upon a formula indicated by reference numeral 60 of FIG. 18. It should be noted that symbol "k" shows a coefficient. As a result, the illuminance fluctuations of the illumination can be normalized.

FIG. 19 schematically shows an arrangement equipped with an illuminance correcting function. In the case that laser light is pulse illumination, 1 pulse, or more pulses should be illuminated within a storage time period during which one pixels is detected. As a consequence, an image acquisition by the image sensor 30 is preferably synthesized with pulse illumination. However, in such a case that an image is detected by the one-directional image sensor 30, the image acquisition by the one-dimensional image sensor 30 is required to be synthesized with a stage for scanning the wafer 1. As one example of realizing this synchronization, while both a signal 241 (X-direction) and another signal 242 (Y-direction) are employed which are obtained by detecting a transport amount of the stage by using a distance measuring device (not shown) such as a linear scale, a synchronization signal 243 generated from a synchronization signal generating device 240 is entered into a pulse control unit 250 in response to a preset image sampling period. A synchronization pulse signal 244 is outputted from the pulse control unit 250 into a laser light pulse oscillating driver 230 in response to the synchronization signal 243, and then, laser light is oscillated in a pulse form from the laser light source 2 by receiving this pulse synchronization signal 244.

Also, from the pulse control unit 250, the synchronization pulse signal 245 is entered into a driver 31 of the image sensor 30, so that such a control operation is carried out in which timing at which the laser light is oscillated from the laser light source 2 may be synchronized with such a timing at which the image is acquired by the image sensor 30. Although not described in FIG. 19, a similar control operation is carried out as to both the laser light source 4 and the image sensor 35.

Furthermore, the synchronization pulse signal 246 is also supplied from the pulse control unit 250 to an illuminance correcting unit 60. The illuminance correcting unit 60 acquires an illuminance detection signal of laser light outputted from the illuminance monitor 55 in synchronism with the timing at which the laser light is oscillated from the laser light source 2 and also the timing at which the image is acquired by the image sensor 30, and then corrects the illuminance fluctuation with respect to the image acquired by the image sensor 30.

With employment of the above-described arrangement, it is possible to solve the temporal/spatial coherence problem occurred by employing the laser in the illumination light source, the interference noise problem caused by the thin film formed on the sample surface, the contrast problem of the background pattern and the brightness, the illuminance fluctuation problem of the pulse illumination light, and the like. Since the F2 laser (wavelength being 157 nm) corresponding to the vacuum ultraviolet light (VUV light) is employed as the light source, not only such a defect whose dimension is larger than, or equal to 50 nm, but also such a very fine pattern defect having a dimension of approximately 20 to 30 nm can be detected in a high sensitivity and also in a high speed. It should also be noted that a pulse oscillation must be performed in a high frequency so as to detect an image in a high speed by employing a pulse oscillation laser light source. This reason is given as follows. That is, in order to detect an image, at least one pulse, or more pulses are required for illumination within a range of the storage time of the image sensor 30.

However, when energy of light which is illuminated on the wafer 1 is high, a pattern formed on the wafer 1 may be damaged. As a consequence, in order to acquire an image of one pixel, this image must be illuminated by using a plurality of pulses. As to the number of these pulses, 30 pulses, or more pulses are required, depending upon a material. As a consequence, in order to detect an image in a high speed (for instance, 50 Gpps [Giga pixel per second]), a pulse oscillation must be carried out in a high frequency. Ideally speaking, while a continuous pulse oscillation may be preferably used, in the case of pulse oscillation, the pulse oscillating frequency higher than, or equal to 50 KHz is required.

Alternatively, a TDI (Time Delay Integration) image sensor may be combined with the above-described arrangement, while this TDI image sensor is capable of prolonging the storage time of the image sensor 30 with maintaining the image acquisition speed. It should be understood that the TDI image sensor corresponds to such a system for storing electron charges of CCD elements which are arranged along a scanning direction of an image in synchronism with a speed at which an optical image of the wafer 1 is scanned, while these electron charges are transferred. To realize the previously explained image detecting speed of 50 Gpps, 2000, or more stages capable of delaying/integrating the electron charges are required. As a result, the high-speed image detecting operation can be realized, and thus, a high throughput of the inspecting apparatus can be realized.

FIG. 20 shows a flow chart for explaining process operations executed in such a case that a pattern defect is inspected by employing the defect inspecting apparatus shown in FIG. 1, which employs the above-explained optical system of the present invention. The laser light 4 emitted from the laser light sources 2 and 4 is conducted into the optical path difference optical system so as to reduce coherences of a plurality of wavelengths (λ1, λ2), and this laser light 4 is again converted into linearly polarized light. This linearly polarized light is converted into elliptically polarized light by employing a wavelength plate, and then, this elliptically polarized light is used via an objective lens to illuminate the sample 1. At this time, illuminance of the illumination light is monitored. Light which has been reflected and diffracted on the sample 1 by this illumination and then has been condensed by the objective lens passes through the previously explained wavelength plate. At this time, the zero-order light corresponding to the direct-reflected light is converted into substantially learly polarized light. Among these plural sets of light, a specific polarized component is conducted to a detection optical path.

In the detection optical path, an optical path is wavelength-split by a dichroic mirror, and optical images are formed on image planes corresponding to the respective wavelengths. These optical images are detected by an image sensor so as to be photoelectrically converted respectively, so that variable-density information is outputted by way of a video signal. This video signal is converted into a digital signal. Next, brightness fluctuations of the image caused by illuminance fluctuations are corrected by employing such a signal for monitoring the illuminance of the illumination light.

Next, a plurality of digital images which have been wavelength-split and detected are synthesized with each other. This synthesized image is entered into a positioning process unit. Also, the synthesized image is also stored in a delay memory, and then is time-delayed in correspondence with pitches to be compared, and thereafter is entered into this positioning process unit. For example, in the case that a die comparison operation is carried out, the positioning process unit executes the positioning operation between the images which have been synthesized to be entered into this positioning process unit, and images of adjoining dies, which have been saved in the delay memory. Next, in the positioning process unit, the images to which the positioning process operations have been accomplished are compared with each other for an inspection purpose, a feature amount of differences is calculated so as to extract a defect, and then, information about the extracted defect is outputted. This defect information to be outputted may contain an image of a defect.

As previously explained, the inspecting apparatus, the managing methods of the inspective result, and the utilizing methods of the inspective results have been described by indicating the various embodiments. However, these indicated examples merely constitute one example of the present invention. Alternatively, other embodiments realized by combining these embodiments with other may be apparently defined within the technical scope of the present invention. For instance, the laser light may be readily replaced by a lamp light source.

Next, FIG. 21 schemaically indicates a system capable of operating a manufacturing line in a high efficiency by effectively utilizing the above-described inspecting apparatus. First, the wafer 1 is conducted to the manufacturing line, and then is processed by a manufacturing apparatus group 29. In an intermediate step where a specific processing operation has been carried out, an inspection is executed by an inspecting apparatus 300 according to the present invention. This inspecting apparatus 300 senses an abnormal state of a pattern which has been manufactured in the preceding steps. In the case of a multi-layer film, these steps are repeatedly carried out. A wafer which has been processed through the above-described process steps is finally accomplished, and then is further processed in post steps (die cutting, formation of lead wires, packaging, and the like), so that the wafer 1 may finally become a product. As to process abnormal states sensed by the respective inspecting apparatus, reasons of these abnormal states and defect solution contents for these abnormal states are analyzed by an analyzing apparatus, if necessary.

In accordance with the present invention, while the inspection results which are sequentially detected and the solution contents are stored in a production information managing system 296, such a system may be constituted by which the abnormal states may be discovered in an earlier stage and may be predicted so as to reduce failure products as small as possible. This system is indicated in FIG. 11. Defect information detected by inspecting apparatus is inputted into both a defect information database 297 and a defect information collation system 292. Also, the defect information collation system 292 may collate information with a yield/manufacturing apparatus information managing system 299.

The production information managing system 296 shown in FIG. 21 is constituted by the defect information database 297, the defect information collation system 298, and the yield/manufacturing apparatus information managing system 299. The defect information database 297 stores thereinto defect information which has been detected after the manufacturing line was initiated. As the data, this defect information database 297 stores thereinto ADC (Auto Defect Classification) results corresponding to inspection results; both-images and coordinate values of defect portions which are detected in real time during inspections; and also, defect feature amounts calculated in the image processing operation.

Also, with respect to these defects, the defect information database 297 stores such information as to defect occurrence reasons, defect solution results, and defect fatality. Also, the defect information collation system 298 collates/retrieves the various sorts of information of the defect information database 297 which have been previously acquired based upon inspection results (ADC result, image of defect portion, coordinate value of defect portion, defect feature amount) which are acquired by the inspection, and thus, judges fatality of the defects. As a result, when it is so judged that the collated defect has a high fatality, the defect information collation system 298 establishes a correlative relationship between this judged defect and the past defect data. In the case that this judged defect owns the correlative relationship with the past defect data, the production information managing system 296 may propose a content of a defect solution with reference to the defect solution information stored in the defect information database 297.

Also, in the case that the judged defect corresponds to such a defect which has not yet occurred in the past, the analyzing apparatus analyzes a cause of this defect, and also analyzes a defect generating apparatus to execute, a defect solution. Also, since the defect information collation system 298 statistically establishes a correlative relationship between the above-described defect information and transitions of yield, maintenance conditions of the manufacturing apparatus, and the like, the defect information collation system 298 may probably disclose a causal relationship between the defect and the yield, and also a causal relationship between the defect and the apparatus condition. As a consequence, the production information managing system 296 can grasp a prediction of the yield and the maintenance conditions of the apparatus, and may take a necessary defect solution in an earlier stage in the case that lowering of the yield may be predicted. Also, since data about these defect occurring conditions and defect solution conditions are sequentially stored into the defect information database 297 and the yield/manufacturing apparatus information managing system 299, reliability of the data as well as reliability of the prediction can be improved.

As has been explained above, in accordance with the present invention, since the present invention can solve the temporal/spatial coherence problem occurred by employing the laser in the illumination light source, the interference noise problem caused by the thin film formed on the sample surface, the contrast problem of the background pattern and the brightness, the illuminance fluctuation problem of the pulse illumination light, and the like, the defects of the patterns can be inspected in the high speed and in the high sensitivities by employing the laser having the large light amount. In particular, since the F2 laser (wavelength being 157 nm) corresponding to the vacuum ultraviolet light (VUV light) is employed as the light source, such a very fine pattern defect having a dimension of approximately 20 to 30 nm can be detected in a high sensitivity and in the high speed.

The invention may be embodied in other specific forms without departing from the spirit or essential characteristics thereof. The present embodiment is therfore to be considered in all respect as illustrative and not restrictive, the scope of the invention being indicated by the appended claims rather than by the foregoing description and all changes which come within the meaning and range of equivalency of the claims are therefore intended to be embraced therein.

What is claimed is:

1. A method for inspecting a defect, comprising the steps of:
   irradiating a pulse laser beam emitted from a pulse-oscillating laser light source to a sample by dark field illumination;
   sensing light reflected from said sample caused by the irradiation of said pulse laser beam by said dark field illumination with a sensor; and
   detecting a defect on said sample by processing a signal output from said sensor;
   wherein said pulse laser beam which irradiates said sample is divided in time into plural pulses from said pulse laser beam emitted from said pulse-oscillating laser light source, and said plural pulses are irradiated to substantially a same position on said sample.

2. A defect inspecting method as claimed in claim 1, wherein a pattern is formed on said sample, and in the step of detecting, a defect of said pattern is detected.

3. A defect inspecting method as claimed in claim 1, wherein said pulse laser beam which irradiates said sample is divided into plural pulses from said pulse laser beam emitted from said pulse-oscillating laser light source by passing through a plurality of optical paths having different optical path lengths from each other.

4. A method for inspecting a defect comprising the steps of:

irradiating a pulse laser beam emitted from a pulse-oscillating laser light source to a sample by dark field illumination;

sensing, with a sensor, light from said sample to which the pulse laser beam is irradiated; and detecting a defect on said sample by processing a signal output from said sensor;

wherein of said pulse laser beam which irradiates said sample is divided in time into plural pulses from said pulse laser beam emitted from said pulse-oscillating laser light source, and amplitudes of said plural pulses are substantially equal to one another.

5. A defect inspecting method as claimed in claim 4, wherein a pattern is formed on said sample, and in the step of detecting, a defect of said pattern is detected.

6. A defect inspecting method as claimed in claim 4, wherein said pulse laser beam which irradiates said sample is divided into plural pulses from said pulse laser beam emitted from said pulse-oscillating laser light source by passing through a plurality of optical paths having different optical path lengths from each other.

7. A defect inspecting method as claimed in claim 4, wherein said sensor is a time delay integration sensor.

8. A method for inspecting a defect comprising the steps of:

irradiating plural laser beams having different wavelengths from each other emitted from plural laser light sources to a sample;

splitting reflection light reflected from said sample to which said plural laser beams are irradiated by each of the plural wavelengths;

sensing each of said split reflection light with sensors;

synthesizing detection signals output from said sensors with each other corresponding to each of the plural wavelengths; and detecting a defect on said sample by processing said synthesized detection signals;

wherein said plural laser beams include at least one pulse laser beam emitted from a pulse-oscillating laser light source, said at least one pulse laser beam being divided in time into plural pulses.

9. A defect inspecting method as claimed in claim 8, wherein a pattern is formed on said sample, and in the step of detecting, a defect of said pattern is detected.

10. A defect inspecting method as claimed in claim 8, wherein said pulse laser beam which irradiates said sample is divided into plural pulses from said pulse laser beam emitted from said pulse-oscillating laser light source by passing through a plurality of optical paths having different optical path lengths from each other.

11. A method for inspecting a defect of a specimen, comprising the steps of:

irradiating a pulse laser beam to a sample, said pulse laser beam being produced by a pulse-oscillating laser light source which emits said pulse laser beam;

sensing light reflected from said sample by the irradiation with a sensor; and detecting a defect having a dimension of 30 nm to 20 nm by processing an output signal from said sensor;

wherein said pulse laser beam emitted from said pulse-oscillating laser light source is so arranged that plural pulses are irradiated to substantially a same portion on said sample within a range of a storage time of said sensor.

12. A defect inspecting method as claimed in claim 11, wherein a wavelength of said pulse-oscillating laser light is 157 nm.

13. A defect inspecting method as claimed in clam 11, wherein said pulse-oscillating laser light source is a vacuum ultraviolet pulse-oscillating laser light source.

* * * * *